United States Patent
Case et al.

(10) Patent No.: US 7,658,759 B2
(45) Date of Patent: Feb. 9, 2010

(54) INTRALUMENALLY IMPLANTABLE FRAMES

(75) Inventors: Brian C. Case, Lake Villa, IL (US); Jacob A. Flagle, Indianapolis, IN (US); Michael L. Garrison, Indianapolis, IN (US)

(73) Assignee: Cook Incorporated, Bloomington, IN (US)

( * ) Notice: Subject to any disclaimer, the term of this patent is extended or adjusted under 35 U.S.C. 154(b) by 472 days.

(21) Appl. No.: 11/487,629

(22) Filed: Jul. 17, 2006

(65) Prior Publication Data

US 2007/0021826 A1    Jan. 25, 2007

Related U.S. Application Data

(63) Continuation-in-part of application No. 10/828,716, filed on Aug. 30, 2004.

(60) Provisional application No. 60/700,852, filed on Jul. 19, 2005, provisional application No. 60/465,141, filed on Apr. 24, 2003, provisional application No. 60/530,781, filed on Dec. 18, 2003.

(51) Int. Cl.
*A61F 2/06* (2006.01)

(52) U.S. Cl. .................................. 623/1.15

(58) Field of Classification Search ....... 623/1.15–1.18, 623/1.24, 1.26, 2.12, 2.14, 2.18
See application file for complete search history.

(56) References Cited

U.S. PATENT DOCUMENTS

| | | | |
|---|---|---|---|
| 5,344,426 A | 9/1994 | Lau et al. ............... 606/198 |
| 5,358,518 A | 10/1994 | Camilli | |
| 5,397,355 A | 3/1995 | Marin et al. ............ 623/12 |
| 5,545,215 A | 8/1996 | Duran | |
| 5,591,197 A | 1/1997 | Orth et al. ............. 606/198 |
| 5,755,781 A | 5/1998 | Jayaraman ............... 623/1 |
| 5,824,045 A | 10/1998 | Alt ....................... 623/1 |
| 5,836,964 A | 11/1998 | Richter et al. .......... 606/194 |
| 5,843,117 A | 12/1998 | Alt et al. .............. 606/194 |
| 5,855,600 A | 1/1999 | Alt ....................... 623/1 |
| 5,855,601 A | 1/1999 | Bessler et al. | |
| 5,876,445 A | 3/1999 | Andersen et al. ........ 623/11 |
| 5,907,893 A | 6/1999 | Zadno-Azizi et al. ..... 29/6.1 |
| 5,957,949 A * | 9/1999 | Leonhardt et al. ....... 623/1.24 |
| 6,033,398 A | 3/2000 | Farley et al. | |
| 6,053,940 A | 4/2000 | Wijay ..................... 623/1 |
| 6,123,721 A | 9/2000 | Jang ...................... 623/1 |
| 6,129,755 A | 10/2000 | Mathis et al. ........... 623/1.15 |

(Continued)

*Primary Examiner*—Alvin J Stewart
(74) *Attorney, Agent, or Firm*—Brinks Hofer Gilson & Lione

(57) ABSTRACT

Implantable frames for use in body passages are provided herein. The implantable frames comprise one or more of certain preferred structural features that are generally applicable to frames comprising a plurality of curved and straight member portions that together define an interior lumen extending along a longitudinal axis between a proximal end and a distal end. The implantable frames have an exterior surface comprising a plurality of openings between the interior lumen and the exterior surface, and preferably include one or more undulating hoop members attached to one or more longitudinal connecting members. The implantable frames can be formed from any suitable material, but preferably comprise material permitting the frame to radially self-expand from a radially compressed configuration to a radially expanded configuration. The implantable frames are useful for endolumenal implantation within a body vessel, for example as a stent or as a support frame of an implantable valve.

19 Claims, 12 Drawing Sheets

U.S. PATENT DOCUMENTS

| | | | | |
|---|---|---|---|---|
| 6,132,460 | A | 10/2000 | Thompson | 623/1.15 |
| 6,132,461 | A | 10/2000 | Thompson | 623/1.15 |
| 6,146,416 | A | 11/2000 | Andersen et al. | 623/1.15 |
| 6,159,237 | A | 12/2000 | Alt et al. | 623/1.11 |
| 6,190,406 | B1 | 2/2001 | Duerig et al. | 623/1.2 |
| 6,200,336 | B1 | 3/2001 | Pavcnik et al. | |
| 6,235,053 | B1 | 5/2001 | Jang | 623/1.15 |
| 6,241,763 | B1 | 6/2001 | Drasler et al. | |
| 6,254,632 | B1* | 7/2001 | Wu et al. | 623/1.15 |
| 6,280,467 | B1 | 8/2001 | Leonhardt | 623/1.16 |
| 6,283,990 | B1 | 9/2001 | Kanesaka | 623/1.11 |
| 6,287,334 | B1 | 9/2001 | Moll et al. | |
| 6,315,793 | B1 | 11/2001 | Bokros et al. | |
| 6,325,819 | B1 | 12/2001 | Pavcnik et al. | |
| 6,328,763 | B1 | 12/2001 | Love et al. | |
| 6,340,366 | B2 | 1/2002 | Wijay | 623/1.13 |
| 6,342,067 | B1 | 1/2002 | Mathis et al. | 623/1.15 |
| 6,348,065 | B1 | 2/2002 | Brown et al. | 623/1.16 |
| 6,355,056 | B1 | 3/2002 | Pinheiro | 623/1.13 |
| 6,425,916 | B1* | 7/2002 | Garrison et al. | 623/2.11 |
| 6,440,163 | B1 | 8/2002 | Swanson et al. | 623/1.23 |
| 6,458,153 | B1 | 10/2002 | Bailey et al. | |
| 6,478,819 | B2* | 11/2002 | Moe | 623/2.18 |
| 6,488,702 | B1 | 12/2002 | Besselink | 623/1.15 |
| 6,503,272 | B2 | 1/2003 | Duerig et al. | |
| 6,508,833 | B2 | 1/2003 | Pavcnik et al. | |
| 6,514,063 | B2 | 2/2003 | Acciai et al. | 425/116 |
| 6,558,415 | B2 | 5/2003 | Thompson | 623/1.16 |
| 6,572,650 | B1 | 6/2003 | Abraham et al. | 623/1.38 |
| 6,598,307 | B2 | 7/2003 | Love et al. | |
| 6,613,086 | B1 | 9/2003 | Moe et al. | |
| 6,632,240 | B2* | 10/2003 | Khosravi et al. | 623/1.13 |
| 6,663,661 | B2 | 12/2003 | Boneau | 623/1.11 |
| 6,676,698 | B2 | 1/2004 | McGuckin, Jr. et al. | |
| 6,678,962 | B1 | 1/2004 | Love et al. | |
| 6,730,117 | B1 | 5/2004 | Tseng et al. | 623/1.16 |
| 6,736,844 | B1* | 5/2004 | Glatt et al. | 623/1.22 |
| 6,786,922 | B2 | 9/2004 | Schaeffer | 623/1.15 |
| 6,821,292 | B2 | 11/2004 | Pazienza et al. | 623/1.15 |
| 6,878,162 | B2 | 4/2005 | Bales et al. | 623/1.15 |
| 6,899,729 | B1* | 5/2005 | Cox et al. | 623/1.13 |
| 6,929,660 | B1* | 8/2005 | Ainsworth et al. | 623/1.15 |
| 6,958,076 | B2 | 10/2005 | Acosta et al. | |
| 6,962,603 | B1 | 11/2005 | Brown et al. | 623/1.15 |
| 6,974,474 | B2 | 12/2005 | Pavcnik et al. | |
| 6,976,995 | B2 | 12/2005 | Mathis et al. | |
| 7,018,403 | B1 | 3/2006 | Pienknagura | 623/1.15 |
| 7,018,406 | B2 | 3/2006 | Seguin et al. | 623/2.1 |
| 7,025,777 | B2 | 4/2006 | Moore | 623/1.15 |
| 7,025,780 | B2 | 4/2006 | Gabbay | |
| 7,060,088 | B1 | 6/2006 | Fischell et al. | 623/1.15 |
| 7,128,756 | B2 | 10/2006 | Lowe et al. | 623/1.15 |
| 7,153,324 | B2 | 12/2006 | Case et al. | |
| 7,160,320 | B2 | 1/2007 | Duran | |
| 7,195,641 | B2* | 3/2007 | Palmaz et al. | 623/2.18 |
| 7,198,646 | B2* | 4/2007 | Figulla et al. | 623/2.1 |
| 7,377,938 | B2* | 5/2008 | Sarac et al. | 623/1.26 |
| 2001/0020183 | A1 | 9/2001 | Jang | 623/1.15 |
| 2002/0010504 | A1 | 1/2002 | Alt | 623/1.15 |
| 2002/0111339 | A1 | 8/2002 | Klausener et al. | 614/183 |
| 2002/0123790 | A1 | 9/2002 | White et al. | 623/1.14 |
| 2002/0138135 | A1* | 9/2002 | Duerig et al. | 623/1.24 |
| 2002/0138138 | A1* | 9/2002 | Yang | 623/2.18 |
| 2002/0188348 | A1* | 12/2002 | DiMatteo et al. | 623/1.24 |
| 2003/0023300 | A1* | 1/2003 | Bailey et al. | 623/1.13 |
| 2003/0093144 | A1 | 5/2003 | Jang | 623/1.15 |
| 2003/0144670 | A1 | 7/2003 | Pavcnik et al. | |
| 2003/0209835 | A1* | 11/2003 | Chun et al. | 264/339 |
| 2003/0220683 | A1 | 11/2003 | Minasian et al. | 623/1.15 |
| 2003/0236568 | A1* | 12/2003 | Hojeibane et al. | 623/1.24 |
| 2004/0024444 | A1 | 2/2004 | Moore | 623/1.15 |
| 2004/0024447 | A1 | 2/2004 | Haverich | |
| 2004/0044401 | A1 | 3/2004 | Bales et al. | 623/1.22 |
| 2004/0093061 | A1 | 5/2004 | Acosta et al. | 623/1.11 |
| 2004/0093073 | A1 | 5/2004 | Lowe et al. | 623/1.15 |
| 2004/0102834 | A1 | 5/2004 | Nakano et al. | 623/1.15 |
| 2004/0106985 | A1 | 6/2004 | Jang | 623/1.16 |
| 2004/0138745 | A1* | 7/2004 | Macoviak et al. | 623/2.36 |
| 2004/0167619 | A1 | 8/2004 | Case et al. | |
| 2004/0225344 | A1 | 11/2004 | Hoffa et al. | |
| 2004/0225356 | A1* | 11/2004 | Frater | 623/2.14 |
| 2004/0243218 | A1 | 12/2004 | Schaeffer | 623/1.15 |
| 2004/0260389 | A1 | 12/2004 | Case et al. | |
| 2005/0075713 | A1* | 4/2005 | Biancucci et al. | 623/1.11 |
| 2005/0075730 | A1* | 4/2005 | Myers et al. | 623/2.18 |
| 2005/0216077 | A1 | 9/2005 | Mathis et al. | |
| 2005/0222661 | A1 | 10/2005 | Case et al. | |
| 2005/0228479 | A1 | 10/2005 | Pavcnik et al. | |
| 2005/0234541 | A1 | 10/2005 | Hunt et al. | |
| 2006/0015178 | A1 | 1/2006 | Moaddeb et al. | |
| 2006/0074480 | A1 | 4/2006 | Bales et al. | 623/1.15 |
| 2006/0095115 | A1* | 5/2006 | Bladillah et al. | 623/1.16 |
| 2006/0116572 | A1 | 6/2006 | Case | |
| 2006/0136045 | A1 | 6/2006 | Flagle et al. | |
| 2006/0178729 | A1 | 8/2006 | Thielen et al. | |
| 2006/0178730 | A1 | 8/2006 | Hill et al. | |
| 2006/0190074 | A1* | 8/2006 | Hill et al. | 623/1.23 |
| 2006/0195004 | A1 | 8/2006 | Jarvik | |
| 2006/0212111 | A1* | 9/2006 | Case et al. | 623/1.24 |
| 2006/0241744 | A1 | 10/2006 | Beith | |
| 2006/0271159 | A1 | 11/2006 | Gregorich et al. | 623/1.15 |
| 2006/0276882 | A1* | 12/2006 | Case et al. | 623/1.24 |
| 2006/0282157 | A1* | 12/2006 | Hill et al. | 623/1.24 |
| 2007/0021826 | A1* | 1/2007 | Case et al. | 623/1.15 |
| 2007/0027535 | A1* | 2/2007 | Purdy et al. | 623/2.18 |
| 2007/0093887 | A1* | 4/2007 | Case et al. | 623/1.24 |
| 2007/0100432 | A1* | 5/2007 | Case et al. | 623/1.15 |
| 2007/0100435 | A1* | 5/2007 | Case et al. | 623/1.24 |
| 2007/0162103 | A1* | 7/2007 | Case et al. | 623/1.13 |
| 2007/0288087 | A1* | 12/2007 | Fearnot et al. | 623/1.24 |
| 2008/0046070 | A1* | 2/2008 | Obermiller et al. | 623/1.24 |
| 2008/0221669 | A1* | 9/2008 | Camilli et al. | 623/1.24 |
| 2009/0177269 | A1* | 7/2009 | Kalmann et al. | 623/1.24 |

\* cited by examiner

INTRALUMENALLY IMPLANTABLE FRAMES

RELATED APPLICATIONS

This application claims the benefit of U.S. provisional patent No. 60/700,852, filed Jul. 19, 2005, and is a continuation-in-part of co-pending U.S. patent application Ser. No. 10/828,716, filed Aug. 30, 2004 and entitled, "Artificial Valve Prosthesis with Improved Flow Dynamics," by Case et al., which in turn claims priority to U.S. Provisional Applications 60/465,141 filed Apr. 24, 2003 and 60/530,781, filed Dec. 18, 2003. All of the above-cited patent applications are incorporated herein in their entirety.

TECHNICAL FIELD

Frames for implantation in body passages are provided herein, as well as methods of treatment relating to the same.

BACKGROUND

Intralumenally implantable frames can be implanted to treat a variety of medical conditions. Implantable frames can maintain patency of body vessels or provide support for a valve or valve leaflets for regulating fluid flow within a body lumen. Implantable frames can be used to treat various conditions. For example, flexible leaflet material can be attached to an implantable frame to form a valve prosthesis useful in providing an artificial valve for treating venous valve insufficiency. In addition, a variety of other implantable prostheses, such as stents, stent grafts and the like, comprise a radially expandable support frame placed within the body to improve the function of a body lumen. Support frames may be implanted in vessels, ducts or channels of the human body and can form part of a valve to regulate fluid flow within a body lumen or as scaffolding to maintain the patency of a body vessel, duct or channel.

Endolumenal prostheses comprising support frames can be placed in a body lumen from a delivery system which includes a catheter. Implantable frames can be intralumenally delivered inside the body by a catheter that supports the stent in a radially compressed form as it is transported to a desired site in a body vessel. Upon reaching the site, the implantable frame can be radially expanded and securably positioned within the lumen of the body vessel, for example by engaging the walls of the body vessel with a portion of the implantable frame. The expansion mechanism may involve expanding the implantable frame radially outward, for example by inflation of a balloon carried by the catheter. When the implantable frame is formed of a material that will self-expand after being compacted, another expansion mechanism involves delivering the implantable frame restrained in a compacted condition and removing the restraint at a point of treatment to allow the implantable frame to self-expand by its own internal elastic restoring force. After expansion of the implantable frame, the catheter delivery system is subsequently withdrawn from the body vessel.

Endolumenally implantable support frames preferably possess sufficient hoop strength to resist collapse of the body vessel, while maintaining a desired degree of radial or longitudinal flexibility to prevent damage to the body vessel.

Implantable frames are subjected to various mechanical forces before, during and after deployment within a body lumen. Before deployment, implantable frames can be compressed and maintained in a compacted form, which can include subjecting the implantable frame to a prolonged inward radial restraining force. During deployment, implantable frames can be subjected to an outward radial expanding force, for example from a balloon expansion or self-expansion process. The implantable frames can also be subjected to an inward radial compressive force upon contact with the body vessel wall during deployment expansion. After deployment, implanted frames can be subject to continued inward radial force from the body vessel wall, in addition to a variety of shearing or tortional forces imparted by movement of the body vessel wall or fluid flow within the body vessel. Uneven mechanical load bearing within an implantable frame can result in uneven wear and distortion of the implantable frame shape, or even failure of structural integrity. In typical sinusoidal and near sinusoidal designs, the bends or radial arcs experience areas of high strain and stress, which can lead to areas of frame fatigue or fracture. However, the stress and/or strain experienced along the length of the radial arc may not be uniform, and there are areas of relatively high stress and/or strain. Therefore, it is desirable to provide implantable frames that more evenly distribute mechanical loads.

Dynamic fluctuations in the shape of the lumen of a body vessel, such as a vein, pose challenges to the design of support frames for implantation within the body vessel. For instance, the flow velocity and diameter of veins do not remain essentially constant at a given systemic vascular resistance. Instead, the shape of vein lumens can fluctuate dynamically in response to the respiration, body position, central venous pressure, arterial inflow and calf muscle pump action of a mammalian subject. The veins also provide the principal volume capacitance organ. For example, an increase of almost 100% in the diameter of the common femoral vein has been observed in human patients simply by rotation of the patient by about 40 degrees, corresponding to a four-fold increase in blood flow volume. Moneta et al., "Duplex ultrasound assessment of venous diameters, peak velocities and flow patterns," J. Vasc. Surg. 8; 286-291 (1988). The shape of a lumen of a vein can undergo dramatic dynamic change as a result of varying blood flow velocities and volumes therethrough, presenting challenges for designing implantable intralumenal prosthetic devices that are compliant to the changing shape of the vein lumen.

Preferably, implantable frames are also configured to minimize undesirable irritation of the lining of a body vessel upon implantation, for example by minimizing the surface area of the frame in contact with the body vessel. However, reducing the surface area of the frame may increase the mechanical stress and strain on particular portions of the frame, particularly bends or arcuate sections. The present disclosure provides implantable frames configured to balance often competing concerns of minimizing potentially irritating external surface area, minimizing foreshortening during radial expansion, and providing a desirable distribution of mechanical loading within the frame during movement of the frame within a dynamic body vessel such as a vein. These implantable frames are particularly useful, for example, as a support for a valve for correcting fluid flow within a body passage, or for opening, dilating and maintaining body vessels and other biological ducts which are at risk of closure or constriction.

Therefore, there is a need for endolumenally implantable medical device frames configured to withstand radial movement upon implantation by desirably distributing the associated mechanical strain on the implanted frame, while also minimizing potential irritation of a body vessel resulting from contact between the body vessel and the external surface of the implanted frame.

DRAWINGS

SUMMARY

Figure 1A:
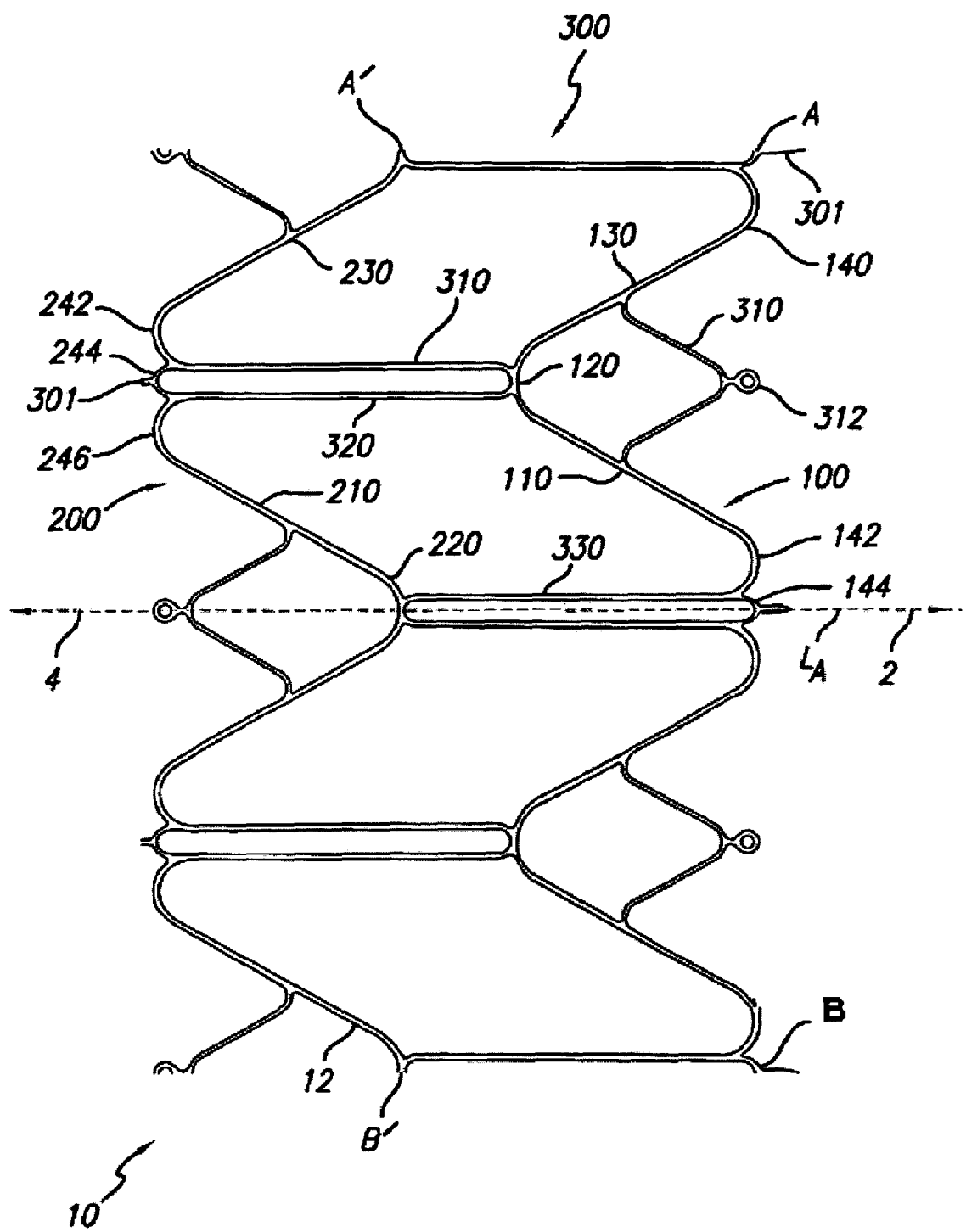
FIG. 1A is a first flat plan view of a first implantable frame.

The present disclosure provides implantable frames configured to balance often competing concerns of minimizing potentially irritating external surface area, minimizing foreshortening during radial expansion, and providing a desirable distribution of mechanical loading within the frame during radial movement of the frame within a dynamic body vessel such as a vein. Implantable frames are provided herein are preferably configured to desirably distribute mechanical strain imparted by radial compression, so as to reduce incidence of strain-induced mechanical failure. These implantable frames are particularly useful, for example, as a support frame for a valve for correcting fluid flow within a body passage, or for opening, dilating and maintaining body vessels and other biological ducts which are at risk of closure or constriction. The implantable frames can be implanted in any suitable body vessel, and are preferably cylindrical structures with substantially open-cell configurations that minimize external surface area, so as to reduce incidence of contact-induced irritation of a body vessel upon implantation.

Accordingly, implantable frames provided herein preferably comprise one or more preferred structural features that desirably distribute mechanical strain during radial movement of the frame, while providing open cell configurations that minimize potential irritation of a body vessel due to contact with the external surface of the frame. Desirably, the frames comprise one or more of the preferred structural features described herein. The preferred structural features are generally applicable to implantable frame designs comprising two or more longitudinally spaced undulating hoop members connected by longitudinal connecting members. Each undulating hoop member can be formed by an array of struts and bends in an S- or Z-shaped configuration joined to form a hoop. Preferably, the undulating hoop members are substantially identical structures joined together by the longitudinal connecting members. The implantable frame can comprise longitudinally adjacent undulating hoop members oriented in opposite longitudinal directions in a "peak-to-peak" orientation relative to one another. Preferably, two or more longitudinal connecting members connect longitudinally adjacent undulating hoop members. More specifically, the longitudinal connecting members can be oriented substantially parallel to one another, and can be positioned to extend between bends in each undulating hoop member. Each longitudinal connecting member preferably connects one bend a distal undulating hoop member to the point of intersection of two or more bends in the proximal undulating hoop member. The longitudinal connecting members are preferably of substantially equal length, and oriented substantially parallel to the longitudinal axis of the frame.

Preferably, the implantable frames comprise one or more of the following preferred structural features. In a first embodiment, each longitudinal connecting member has a substantially equal length and the ratio of the length of the longitudinal connecting members to the length of the frame is between about 1.5 and 2.0, preferably between 1.60 and 1.75. In a second embodiment, the plurality of longitudinal connecting members comprise two or more pairs of closely spaced parallel longitudinal connecting members of substantially equal length configured so that the distance between each pair of closely spaced longitudinal connecting members is less than 25%, preferably less than 15%, of the length of the longitudinal connecting members. Circumferentially adjacent pairs of closely spaced longitudinal can be staggered with respect to one another. Preferably, the total number of longitudinal connecting members in the implantable frame is greater than the total number of struts in each of the two undulating hoop members attached to the longitudinal connecting members. In a third embodiment, the orientation of each strut of the undulating hoop member with respect to an attached longitudinal connecting member defines a strut angle that is between about 145° and about 155°, defined within a closed cell of defined by the frame, although frames having other strut angles are also provided. In a fourth embodiment, the hoop members preferably comprise more bends on one longitudinal end of the hoop than on the opposite longitudinal end. For example, a hoop member may comprise (n) struts, connected to up to (n/2) bends on the distal side of a hoop member, and (n) or greater bends, preferably up to (3n/2) on the proximal side of the hoop member, with (n) being an even integer of 2 or greater, preferably 2-12. In a fifth embodiment, the implantable frame is characterized by two or more symmetry planes containing the longitudinal axis of the implantable frame. The implantable frame preferably has (m) symmetry planes, where (m) is preferably an integer of 1 to 6, more preferably 1 to 3 and most preferably 2 or 3. In a sixth embodiment, the frame comprises a proximal undulating hoop member with a first bend having a semi-circular configuration extending between the first longitudinal connecting member and the first strut, the first bend subtending an arc having a radius centered on the distal side of the proximal hoop member. More preferably, hoop members comprises bends configured as arc segments that desirably distribute mechanical stress and strain during radial movement of the frame.

The implantable frames may also be described with respect to open cells defined along the ablumenal (exterior) surface of the frame. Accordingly, implantable frames typically comprise a plurality of curved and straight member portions that together define an interior lumen extending along a longitudinal axis between a proximal end and a distal end. Preferably, the interior lumen and the exterior surface are both substantially cylindrical. The implantable frames can have an exterior surface comprising a plurality of openings between the interior lumen and the exterior surface. The openings are preferably bounded by portions of the implantable frame. The implantable frame can define a plurality of openings each bounded by a pair of parallel longitudinal connecting struts, a portion of a proximal undulating hoop member and a portion of a distal undulating hoop member. In another embodiment, the implantable frame defines pairs of interstitial openings having mirror image configurations with respect to one another. The plurality of cells can also include pairs of identical load abatement cells bounded by pairs of closely spaced longitudinal connecting members. The circumference of the implantable frame can comprise non-adjacent interstitial openings having mirror image configurations, and non-adjacent identical load abatement openings. Preferably, the implantable frame has (n) pairs of mirror image interstitial openings and (n) pairs of identical load abatement openings, where (n) is an integer of 1 to 12, preferably 1 to 6 and most preferably 2 or 3. The implantable frame also preferably has the same number of pairs of mirror image interstitial openings and symmetry planes containing the longitudinal axis (n=m).

DETAILED DESCRIPTION

Although the following discussion, along with the figures, describes illustrative embodiments, those skilled in the art will understand that variations and combinations of the described embodiments are also disclosed herein.

The terms "implantable frame" and "frame" are used interchangeably to refer to the structures disclosed herein to one of skill in the art. Preferably, the frames are configured for implantation within a body vessel.

The terms "proximal" and "distal" are used to connote a direction or position relative to each other. Unless otherwise indicated, the recitation of "proximal" or "distal" portions of a frame does not refer to any particular orientation of the implantable frame within a body. The implantable frames described herein can be used in many different body lumens, including both the arterial and venous system, and can be implanted in any suitable orientation within the body.

A frame "perimetrically defining" an opening means that substantially the entire perimeter of the opening is defined by portions of the frame. A frame opening "bounded" by a specified portion of the frame means that at least part of the perimeter of the opening is defined by the specified portion of the frame. For example, an implantable frame can comprise an opening between a substantially cylindrical exterior surface and a substantially cylindrical interior lumen that are bounded by a specified portion of the implantable frame may also be perimetrically defined by a combination of the specified portion of the implantable frame and other portions of the implantable frame.

The term "circumferential" or "circumferentially" refers to a direction or displacement measured along the exterior surface area of an assembled implantable frame in the expanded configuration that is transverse to the longitudinal axis of the implantable frame. The recitation of a first structural feature "circumferentially adjacent" to a second structural feature means that the first structural feature is the nearest first structural feature to the second structural feature when moving circumferentially along the exterior surface of an implantable frame. The term "circumferential distance" means distance measured along the exterior surface of an implantable frame in the expanded configuration.

The term "longitudinal" or "longitudinally" refers to a direction measured along the longitudinal axis of the implantable frame. The term "longitudinally opposite" means positioned in a distal or proximal direction along the exterior surface of an implantable frame parallel to the longitudinal axis of the implantable frame. The recitation of a first structural feature "longitudinally adjacent" to a second structural feature means that the first structural feature is the nearest first structural feature to the second structural feature when moving longitudinally along the exterior surface of an implantable frame. The term "longitudinal distance" means a distance or displacement measured parallel to the longitudinal axis of an implantable frame in the expanded configuration, measured along the exterior surface area of the implantable frame.

The term "arcuate" refers to a curved structure or portion thereof.

The term "semi-circular" refers to an arcuate structure forming a portion of a circle.

The term "symmetrically positioned" refers to a similarity in size, shape, or relative position of corresponding parts.

The term "superelasticity" is used herein to describe the property of certain shape memory alloys to return to their original shape upon unloading after a substantial deformation while in their austenitic state. Superelastic alloys can be readily strained while in their austenitic state with minimal plastic deformation. Alloys that show superelasticity may also undergo a thermoelastic martensitic transformation.

Implantable Frame Embodiments

Implantable frames provided herein are preferably configured to desirably distribute mechanical strain imparted by radial compression, so as to reduce incidence of strain-induced mechanical failure. The implantable frames can be implanted in any suitable body vessel, and are preferably cylindrical structures with substantially open-cell configurations that minimize external surface area, so as to reduce incidence of contact-induced irritation of a body vessel upon implantation. Preferably, the frames are placed in a body vessel from a catheter delivery system, and can function in a manner suitable for an intended use, including a stent, or a portion of a valve or stent graft. The implantable frames are desirably configured to provide enough circumferential rigidity and hoop strength to maintain patency of a body vessel, to resist recoil of a body vessel, while maintaining sufficient flexibility to permit endolumenal delivery and to prevent or minimize undesirable irritation or trauma to the lining of the body vessel.

Figure 1B:
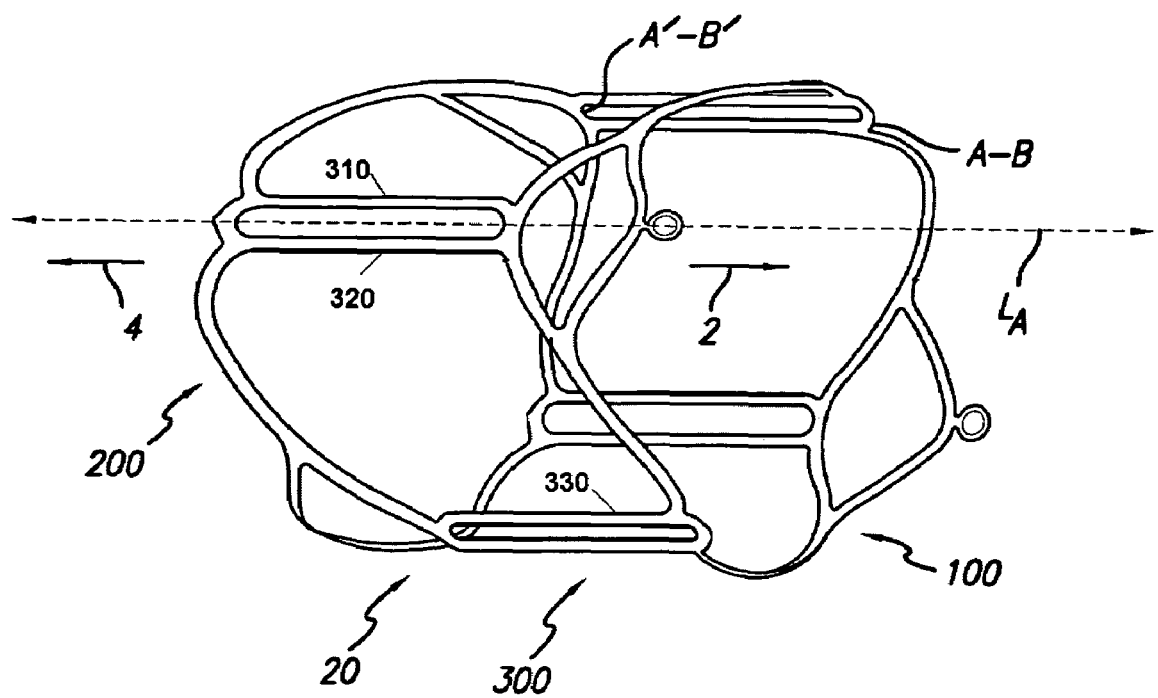
FIG. 1B is a perspective view of the assembled first implantable frame of FIG. 1A in the assembled configuration.
Figure 1C:
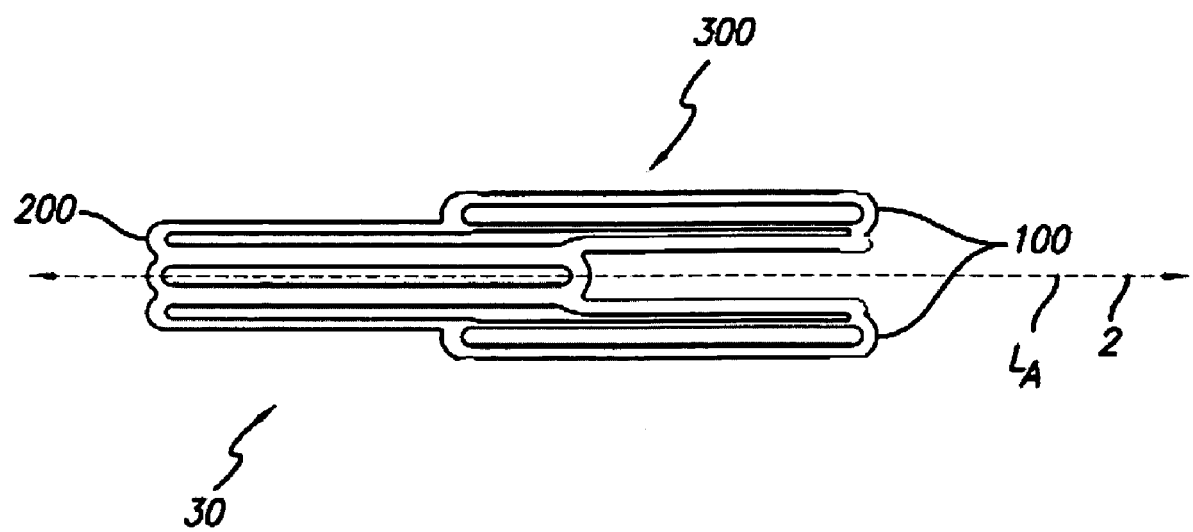
FIG. 1C is a side view of the assembled first implantable frame of FIG. 1A and FIG. 1B in a compressed configuration.

Preferred implantable frames include one or more structural features described in various embodiments herein. These structural features relate generally to the configuration of implantable frames that include two or more undulating hoop members joined by a plurality of longitudinal connecting members. Referring to the implantable frame 12 as shown in FIG. 1A-1C, a proximal undulating hoop member 100 is connected to a distal undulating hoop member 200 by a plurality of longitudinal connecting members 300. Preferably, the undulating hoop members are the same or substantially similar. In frame 12, the proximal undulating hoop member 100 is longitudinally adjacent to the distal undulating hoop member 200, but is oriented in the opposite direction. Most preferably, the frames assume a radially expanded configuration having a pair of longitudinally adjacent radially compressable undulating (i.e., sinusoidal) hoop members connected by a plurality of substantially parallel longitudinal connecting members.

To illustrate certain preferred frame structures, certain structural features of the implantable frames may be discussed herein with reference to flat plan schematic views. Flat plan schematic view of an implantable frame, such as FIG. 1A, are two dimensional representations of an implantable frame obtained by theoretically bisecting the implantable frame parallel to its longitudinal axis, "unrolling" the frame and pressing the implantable frame into a flat configuration. Any flat plan view can be schematically converted into an assembled view of the implantable frame by "rolling" the two transverse edges out of the plane of the flat plan view and joining portions of the transverse edges of the frame to form a three dimensional assembled implantable frame. The above discussion of how to convert a flat plan view to an assembled view does not, however, relate to or suggest any limitation with respect to any particular method for manufacturing the implantable frame, which is discussed below. FIG. 1A shows an unrolled flat plan view 10 of the implantable frame 12. The first implantable frame 10 is oriented along a longitudinal axis $L_A$, having a proximal direction 2 and distal direction 4. The flat plan view 10 of FIG. 1A can be converted to an assembled configuration 20 shown in perspective view of FIG. 1B by theoretically "rolling" the frame around the longitudinal axis $L_A$ so as to "connect" portions of the implantable frame 12 between point A and point B at the proximal edge of the implantable frame 12 and point A' and point B' at the distal end of the implantable frame 12, respectively. Reference to the assembled configuration 20 does not refer to the method of assembling the frame 12 in this configuration, but refers instead to the preferred frame configuration. Preferably, the implantable frame 12 is manufactured without manipulating the frame 12 in the flat plan view 10. Most preferably, the implantable frame 12 is produced by laser cutting a tube of self-expanding material in a radially compressed configuration, and permitting the frame to expand to assume the assembled configuration 20 shown in FIG. 1B. Alternatively, a sheet of suitable material can be cut to form a frame in a planar configuration shown in the flat plan view 10 in FIG. 1A, which can be rolled into the assembled configuration of view 20 by joining to itself by any suitable means, as indicated above. FIG. 1C is a side view of the frame 30 in a radially compressed configuration 30, formed by radially compressing the frame in the assembled configuration 20 in FIG. 1B.

The implantable frame can comprise a pair of undulating hoop members oriented in opposite longitudinal directions and in a "peak-to-peak" orientation relative to one another. In a "peak-to-peak" configuration, the longitudinal connecting members have substantially the same length and longitudinally adjacent struts on two different connected, longitudinally adjacent, undulating hoop members are substantially parallel. For example, the implantable frame 12 has a "peak-to-peak" configuration, with the proximal undulating hoop member 100 oriented in the opposite longitudinal direction from the distal undulating hoop member 200. The longitudinal distance between adjacent undulating hoop members remains substantially constant throughout the frame in the "peak-to-peak" configuration. Alternatively, in a "peak-to-valley" orientation, the longitudinal connecting members typically alternate between one of two lengths (a long and a short length), as the longitudinal distance between adjacent undulating hoop members is different in different parts of the frame in the "peak-to-valley" configuration. Furthermore, longitudinally adjacent struts on adjacent undulating hoop members are oriented in different directions in a "peak-to-valley" orientation.

Each undulating hoop member is formed by an array of struts and bends joined to form a closed hoop structure. For example, the proximal undulating hoop member 100 includes a first strut 130 joined to a first bend 140 and a second bend 120, a second strut 110 between the second bend 120 and a third bend 142, and a third bend 144 joined to the second bend 120. Similarly, the distal undulating hoop member 200 includes a first strut 230 joined to a first bend 242, a second bend 244 joined to the first bend 242, a third bend 246 joined to the second bend 244, and a second strut 210 between the third bend 246 and a fourth bend 220. An undulating hoop member can optionally further comprise one or more bridging members attached to two struts and bridging a bend joining the two struts of a single hoop member. Additional members can facilitate distribution of a mechanical load or provide or enhance other desirable properties of the frame. For example, as shown in FIG. 1A, the proximal undulating hoop member 100 further comprises a first bridging member 310 extending in an undulating fashion between the first strut segment 130 and the second strut segment 110.

The proximal undulating hoop member 100 comprises an array of four struts of equal length, including the first strut 130. Similarly, the distal undulating hoop member 200 comprises an array of four struts of equal length, including the first strut 230, and the second strut 210. The struts are preferably substantially straight, but can bow when the frame is subject to mechanical force depending on the material selected for the frame. Preferably, all of the struts are of the same shape, length and cross sectional area within an undulating hoop member.

Each bend is preferably arcuate, with rounded inflection points such as the first inflection point, but can also be more pointed at the inflection point. The bends can have the same or a different configuration. Preferably all of the bends within an undulating hoop member are substantially rounded in shape. The bends of each undulating hoop member 100, 200 are positioned along the proximal side 2 or distal side 4 of each hoop member 100, 200. Each hoop member 100, 200 comprises a first array of bends on the proximal side 2 ("proximal bends"), and a second array of bends on the distal side 4 ("distal bends"). Preferably, each hoop member 100, 200 includes more bends on one side than the other. The proximal undulating hoop member 100 has four bends along the proximal end along the proximal direction 2 and two bends along the distal end, while the distal undulating hoop member 201 has four bends along the distal end in the distal direction 4 and two bends along the proximal end. For example, an undulating hoop member can comprise a first array of (n) bends at one end and a second array of up to (n/2) bends at the opposite end, where (n) is an integer. The integer (n) is preferably an even integer of 4-12, most preferably 4, 6, or 8. For example, in the implantable frame 12, the proximal undulating hoop member 100 and the distal undulating hoop member 200 each include four struts and eight bends. The proximal undulating hoop member 100 comprises an array of six proximal bends on the proximal side 2 of the undulating hoop member 100, including the first bend 140, the third bend 142, and the fourth bend 144. The fourth bend 144 is shaped differently from the third bend 142 and the first bend 140. The proximal undulating hoop member 100 also includes an array of two distal bends on the distal side 2 of the proximal undulating hoop member 100, including the second bend 120. Similarly, the distal undulating hoop member 200 comprises an array of six distal bends on the distal side 4 of the distal hoop member 200, including the first bend 242, the second bend 244, and the third bend 246, as well as an array of two proximal bends on the proximal side 2, such as the fourth bend 220. Accordingly, the proximal hoop member 100 includes six proximal bends (n=6) and two distal bends (n/3=2), while the distal hoop member 200 includes six distal bends (n=6) and two proximal bends (n/3=2).

Figure 2:
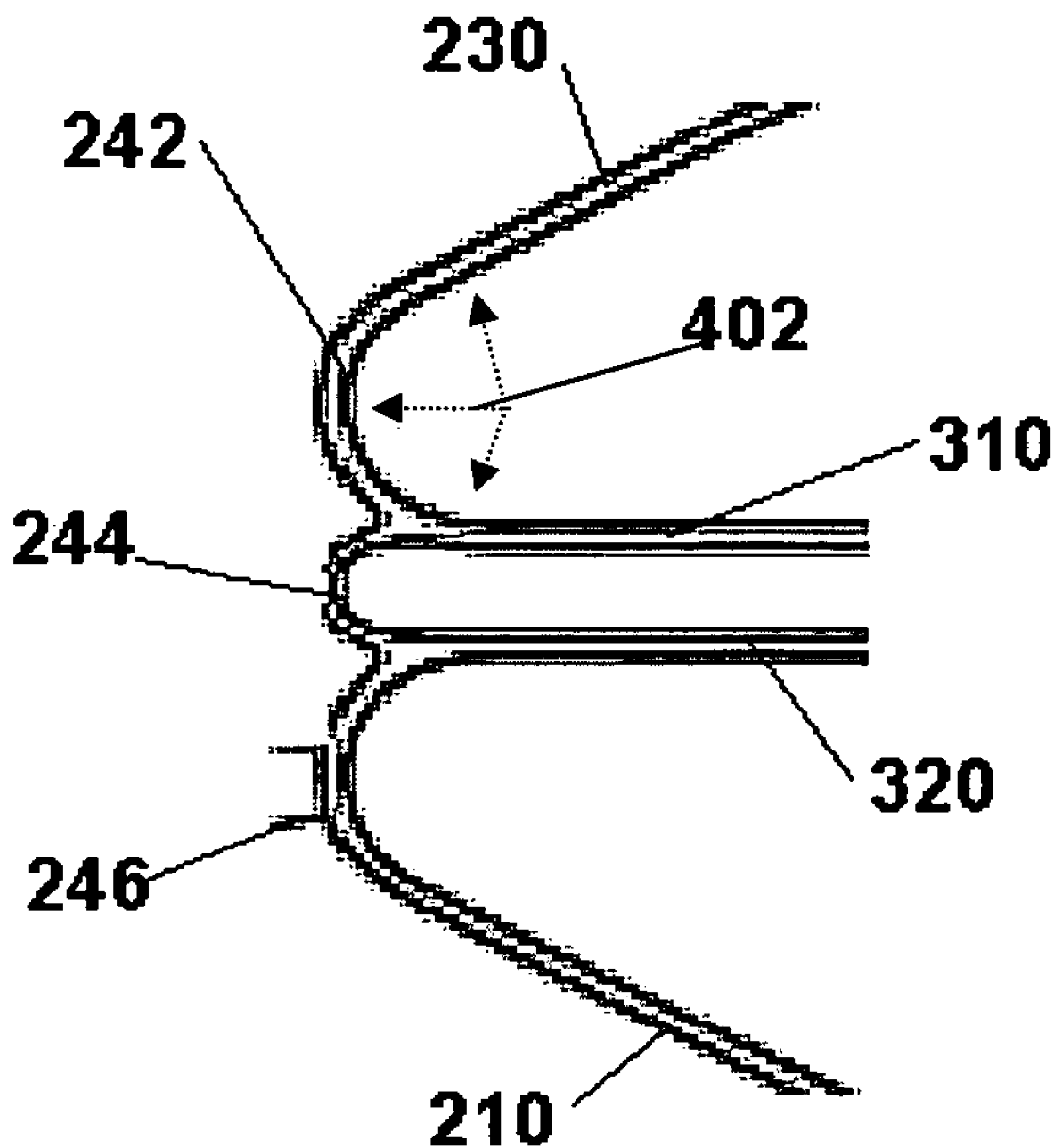
FIG. 2 is a detailed view of a portion of the first implantable frame of FIG. 1A.

The bends can have any suitable configuration, including arcuate or "V"-shaped. Preferably, the bends have an arcuate, semi-circular configuration. It is believed that the semi-circular arcuate configuration desirably distributes mechanical stress associated with radial expansion or compression of the frame. FIG. 2 shows a detailed view of a portion of the first frame 12, showing the first bend 242 and the second bend 244 connected to a portion of the first longitudinal connecting member 310 and a portion of the second longitudinal connecting member 320 connected to the second bend 244 and the third bend 246. The first bend 242 extends from the first strut 230 to the first longitudinal connecting member 310 and has a semi-circular configuration forming an arc at a first hypothetical radius 402. The first hypothetical radius 402 is positioned between the proximal hoop member 200 and the distal hoop member 100 (which are shown in FIG. 1A). The arc of the first bend 242 preferably subtends an angle of between about 5 and 45 degrees between the first longitudinal connecting member 310 and the first strut 230, including angles of about 10, 15, 20, 25, 30, 35, and 40, but preferably about 15-35 degrees.

The undulating hoop members are joined together by longitudinal connecting members. Referring again to FIGS. 1A-1C, the implantable frame 12 comprises a proximal undulating hoop member 100 connected to a distal undulating hoop member 200 by an array of longitudinal connecting members 300, including a first longitudinal connecting member 310 and a second longitudinal connecting member 320. Referring to FIG. 1B, the second longitudinal connecting member 320 is circumferentially adjacent to the first longitudinal connecting member 310 on one side, and longitudinally adjacent to the third longitudinal connecting member 330 on the opposite side. Each longitudinal connecting member preferably connects one bend a distal undulating hoop member to the point of intersection of two or more bends in the proximal undulating hoop member. For example, the first longitudinal connecting member 310 extends from the first bend 120 of the proximal undulating hoop member 100 to join to point of intersection of the first bend 242 and the second bend 244 of the distal undulating hoop member 200. Similarly, the second longitudinal connecting member 320 extends from the first bend 120 of the proximal undulating hoop member 100 to join to point of intersection of the second bend 244 and the third bend 246 of the distal undulating hoop member 200. Preferably, the longitudinal connecting members are of substantially the same length and have a substantially constant and substantially identical cross section throughout their entire length. Preferably, the longitudinal connecting members are substantially straight. All of the longitudinal connecting members 300 are preferably oriented substantially parallel to one another, and are positioned to connect bends in each undulating hoop member. In preferred embodiments, the longitudinal connecting members 300 are substantially parallel to the longitudinal axis of the implantable frame $L_A$.

Preferably, the total number of longitudinal connecting members 300 connecting a pair on longitudinally adjacent hoop members 100, 200 in frame 12 is equal to or less than the total number of struts in both of the undulating hoop members 100, 200. More preferably, when a pair of longitudinally adjacent undulating hoop members comprise a total of (y) struts, then from (y/2) to (y) longitudinal connecting members connect the pair of longitudinally adjacent undulating hoop members, where (y) is an integer. The integer (y) is preferably 2 to 24, more preferably 4, 6, 8 or 10, most preferably 4 or 6. For example, the first longitudinal connecting member 310 extends from the first bend 120 of the proximal undulating hoop member 100 and the distal undulating hoop member 200 together include a total of eight struts (y=8) and are preferably connected by 4, 5, 6, 7 or 8 longitudinal connecting members.

The array of longitudinal connecting members can comprise two or more longitudinal connecting members that are arranged in a longitudinally staggered configuration, whereby at least one longitudinal connecting member is positioned closer to the proximal end of the frame relative to a circumferentially adjacent longitudinal connecting member of substantially the same length. The longitudinal connecting members are preferably either proximal longitudinal connecting members or distal longitudinal connecting members. Preferably, each proximal longitudinal connecting member is attached to at least one bend of a proximal array of bends of an undulating hoop member; each distal longitudinal connecting member is preferably attached to at least one bend of a distal array of bends of an undulating hoop member. For example, the second longitudinal connecting member 320 is longitudinally staggered with respect to a longitudinally adjacent third longitudinal connecting member 330, but not with respect to the other longitudinally adjacent first longitudinal connecting member 310.

The implantable frames can optionally further comprise various other structural elements, such as additional reinforcing members, various structures or structural features for securing the frame within a body vessel, or markers for remotely detecting the position and orientation of the frame in the body vessel. For example, implantable frames may further comprise one or more bridging members extending between portions of a single undulating hoop member. Preferably, the frame comprises bridging members attached to the proximal undulating hoop member 100 and/or the distal undulating hoop member 200. For example, the implantable frame 12 as shown in FIGS. 1A-4 defines a plurality of bridging members 310 defining bridging openings 550 in FIG. 4. In addition, in some embodiments, an implantable frame can comprise additional circumferential reinforcing members joining two circumferentially adjacent longitudinal connecting members. The number, position and orientation of one or more reinforcing members can be selected to provide desired properties to the frame, such as improved load distribution or load bearing properties. The shape, cross sectional area and material of a circumferential reinforcing member can be selected by one skilled in the art to provide a frame with desired properties. In one embodiment, the frame comprises a circumferential reinforcing member connecting a proximal longitudinal connecting member to a circumferentially adjacent distal longitudinal connecting member. Preferably, the circumferential reinforcing member is formed from the same material as and has substantially the same cross sectional area as the longitudinal connecting member.

The frame can optionally include a variety of structures or modifications incorporated in or attached to the frame, to secure the frame within a body vessel upon implantation therein. For example, pointed barbs can be attached to or formed in the frame. In one embodiment, barbs can be formed in or joined to one or more bends in undulating hoop members. For example, the implantable frame 12 comprises a plurality of barbs 301. Other structures or structural modifications for anchoring the frame in a body vessel are known in the art, and include without limitation, forming portions of the frame with barbs, perforations, bioadhesives, roughened surfaces, or heating the frame or portions thereof to bond the frame to the body vessel wall.

Preferably, the implantable frames are expandable between a compressed configuration and an expanded configuration.

In some embodiments, the implantable frames are formed from a material that self-expands radially outward from the compressed configuration to the expanded configuration when the implantable frame is not radially restrained. In other embodiments, the implantable frame can be radially expanded by applying an outward radial force from within the interior lumen of the implantable frame, for example by inflation of a balloon positioned inside the interior lumen of the implantable frame in the compressed state. FIG. 1B is a perspective view of the implantable frame 12 in an expanded configuration 20. The expanded assembled first implantable frame 20 shows the proximal undulating hoop member 100 connected to the distal undulating hoop member 200 by the array of longitudinal connecting members 300. The expanded configuration 20 of the implantable frame 12 is oriented along a longitudinal axis $L_A$, having a proximal direction 2 and a distal direction 4. FIG. 1C is a side view of the assembled first implantable frame 10 shown in FIG. 1A in the compressed configuration 30.

Preferred Frame Configurations

Typically, implantable frames are subjected to periodic and repeated radial compression and expansion upon implantation. For example, frames implanted in the vascular system are subject to radial movement resulting from periodic blood flow, and accompanying changes in fluid flow rate and pressure due to the approximately 8 million heart beats of a human patient every year. Frames in veins may undergo radial compression as veins dilate or prolapse in response to changes in body activity or position, in addition to pulsatile blood flow. The stress and/or strain experienced along the length of an implantable frame during radial compression or expansion is typically not uniform, and there are areas of relatively low stress and/or strain. Implantable frames comprising sinusoidal hoop members, the radial arcs often experience areas of high mechanical strain and stress during radial compression and expansion, which can lead to fatigue and even failure (e.g., fracture of the frame). One method of predicting the stress and/or strain state in the structure is finite element analysis (FEA), which utilizes finite elements (discrete locations). "Finite element analysis" is a mathematical approach wherein a frame structure is segmented into many pieces that have closed form solutions. That is, each piece can be defined by a linear equation, and hence is a "finite element." Collectively, the linear equations of the pieces form a system of equations that are simultaneously solvable. Computer programs for simulating finite element analysis in various applications exist. For example, design engineers use finite modeling programs. Typically, many thousands of elements are created to model a subject object and in particular three-dimensional objects. For each element, there is geometric information such as an x-y-z coordinate at a point in the element, an element type, material property, stress value, displacement, thermal value, etc. Such information is definable by linear equations for the elements. To that end, finite analysis is employed to model the subject object. Examples of finite modeling programs include: ABAQUS by Hibbitt, Karlsson, and Sorensen, Inc. of Pawtucket, R. I., ANSYS by Swanson Analysis Systems Inc. of Houston, Pa.: SUPERTAB by Structural Dynamics Research corp. of Ohio; and PATRAN by PDA Engineering of Costa Mesa, Calif. Typical FEM software comprises modules to create an element mesh from a plurality of device segments (e.g., to create a representation of a simulated device), to analyze a defined problem, and to review results of modified parameters on device design.

By using FEA to model the mechanical strain experienced by the first frame 12 in the assembled configuration 20 shown in FIG. 1B, preferred frame configurations were developed that desirably distribute mechanical load (e.g., strain or stress) imposed by periodic radial contraction and expansion. These preferred frame configurations therefore permit the selection of frame configurations with a lower probability of fracture and irritation of the vessel.

Preferred frame designs provide improved and more uniform strain distribution. Certain critical frame regions showed higher strain during FEA analysis. These included the bends of the proximal and distal hoop members as well as the points of attachment of bridging members to either hoop member. In general, strain was largely concentrated in radial arcs, flexural arcs and/or flexural struts. In bend areas where initial stress and/or strain were high, the geometry of the bend was changed to reduce the maximum stress and/or strain in these areas. In particular, the distal bends of the distal hoop member 200 and the proximal bends of the proximal hoop member 100 were areas of high mechanical loading. By configuring these bend arrays as semi-circular arcuate structures with a radius positioned between the two hoop members, the maximum amount of strain on these bends was reduced. In addition, the cross sectional area of the bridging members 310 was reduced compared to the cross sectional area of the rest of the frame. For example, a bridging member 310 cross sectional area may be about 30-40% compared to the cross sectional area of the hoop member to which it is attached. Preferred frame geometries also allow radial compression of the frame (crimping) around a conventional delivery balloon catheter, resulting in a low profile (e.g., 6 F) guiding catheter compatible stent delivery system. Percentage of axial shortening upon expanding the balloon is preferably minimized, and can be less than 5%.

Figure 3:
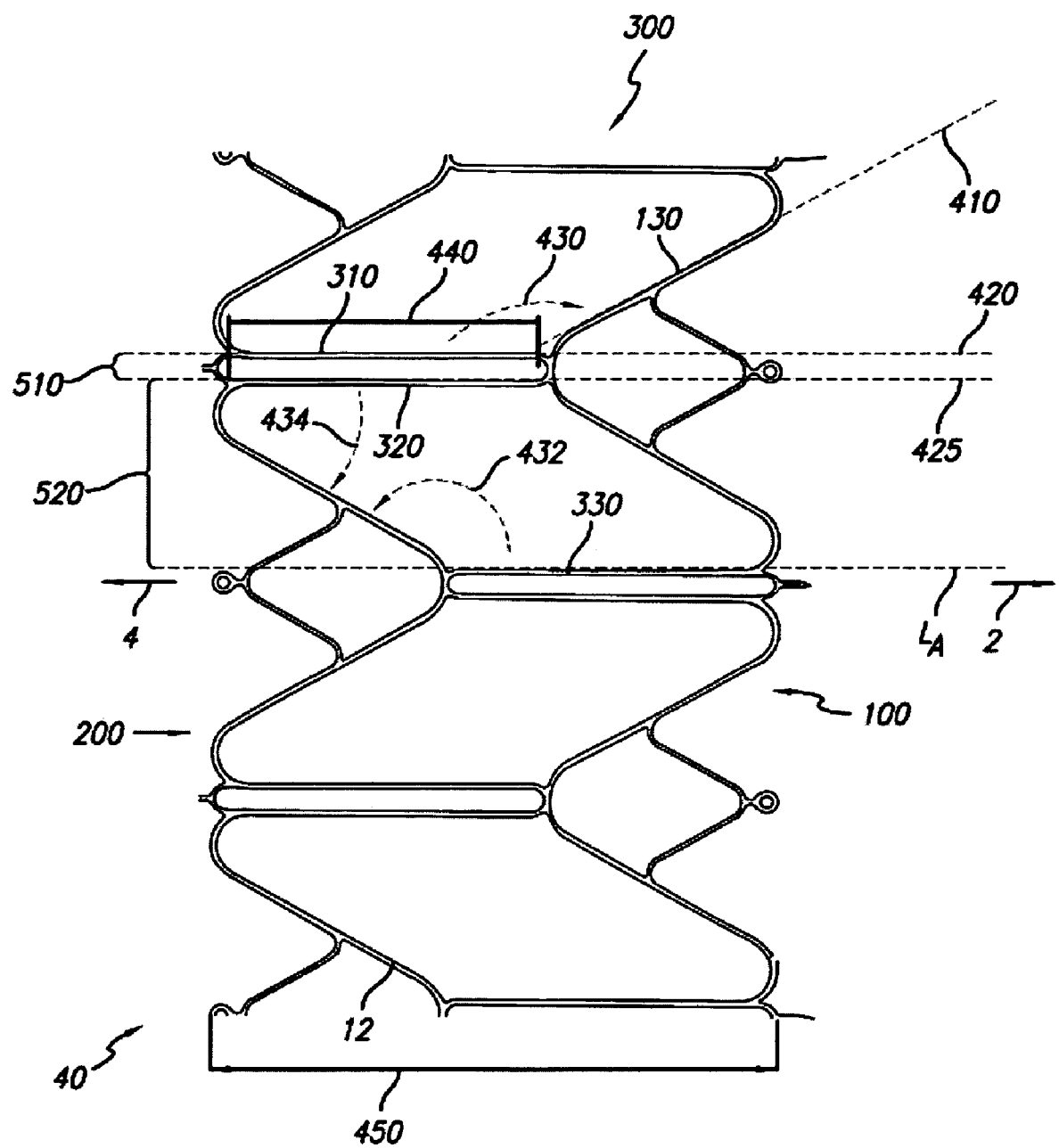
FIG. 3 is a second flat plan view of the first implantable frame.

Accordingly, preferred embodiments relate to implantable frames characterized by one or more structural relationships between the longitudinal connecting members and portions of the undulating hoop members. FIG. 3 is a flat plan view 40 of the implantable frame 12 indicating certain structural relationships of the embodiment illustrated in FIGS. 1A-1C.

In a first embodiment, each longitudinal connecting member has an equal length and the ratio of the length of the frame to the length of the longitudinal connecting members is between about 1.50 and about 2.00, preferably between 1.60 and 1.75. The length of the frame refers to the distance from inflection point of the most distal bend in the distal hoop member to the inflection point of the most proximal bend in the proximal hoop member. Other suitable ratios between the length of the frame and the length of the longitudinal connecting members include 1.60, 1.70, 1.75, 1.80, 1.90, and 2.00, including ratios of 0.05 therebetween. For example, in FIG. 3, each of the longitudinal connecting struts 300, including the first longitudinal connecting strut 310 and the second longitudinal connecting strut 320, have equal lengths. The length 440 of the longitudinal connecting struts 300 can be any length suitable for implantation in a body vessel, such as about 10-15 mm. The length 450 of the implantable frame 12 is measured along the longitudinal axis $L_A$ from the inflection point of the most distal bend of the distal undulating hoop member to the inflection point of the most proximal bend of the proximal undulating hoop member, such as the first distal bend 242. Preferably, the inflection points of the distal bends of the distal undulating hoop member 200 are all aligned with respect to each other, as in frame 12 shown in FIG. 3, and the inflection points of the proximal bends in the undulating hoop member 100 are similarly aligned at the opposite end of the implantable frame 12. The implantable frame can have any length suitable for implantation in a body vessel, such as about 16-25 mm, preferably between about 1.5 and 2.0 times the length of the longitudinal connecting members. The length 450 of the implantable frame 12 is about 1.67 times the length 440 of the longitudinal struts 300 (i.e., the ratio of the length 450 of the implantable frame 12 to the length 440 of the longitudinal struts 300 is about 1.67). Optionally, the frame 12 can also include additional hoop members positioned between the proximal hoop member 100 and the distal hoop member 200. Preferably, for a self-expanding frame, the overall frame length is selected to be about 1.5-2.5 times, more preferably about 2.0 times, the diameter of the body vessel at the site of implantation therein. The overall length of a frame having the configuration 20 shown in FIG. 1B typically varies according to the overall diameter. The length of the longitudinal connecting members is preferably about 90-150%, more preferably about 110-130%, and most preferably about 120% of the diameter of the frame. One skilled in the art will appreciate the geometric design relationships that exist between selecting the length of the implantable frame and the length of the longitudinal connecting members, and other design parameters such as diameter and circumference.

In a second embodiment, the plurality of longitudinal connecting members comprise two or more pairs of closely spaced parallel longitudinal connecting members of equal length configured. Recitation of "closely spaced" indicates that the distance between each pair of closely spaced longitudinal strut members is less than 25%, preferably less than 15%, of their length. Preferably, two closely spaced longitudinal connecting members are substantially equal in length and substantially parallel to the longitudinal axis of the frame. In FIG. 3, the first longitudinal connecting strut 310 and the second longitudinal connecting strut 320 together form a pair of closely spaced parallel longitudinal connecting members. A first longitudinal connecting strut axis 420 bisects the first longitudinal connecting strut 310 in parallel to the longitudinal axis $L_A$, and a second longitudinal connecting strut axis 425 bisects the second longitudinal connecting strut 425 in parallel to the longitudinal axis $L_A$. The second longitudinal connecting strut 320 is positioned at a first circumferential distance 510 from the first longitudinal connecting strut 310, and a second circumferential distance 520 from the third longitudinal connecting strut 330. The first circumferential distance 510 is the distance between the closely spaced longitudinal struts 310, 320 is preferably less than 25% of the length 440 of the closely spaced pair of longitudinal struts 310, 320. The circumferential distance between closely paired circumferentially adjacent longitudinal connecting members is preferably less than about 30%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1% of their total length, including percentages between any of these percentages. In FIG. 3, the first circumferential distance 510 is between about 9-10% of the length 440 of the closely spaced pair of longitudinal struts 310, 320.

In some preferred embodiments, an implantable frame comprises a longitudinally staggered array of paired longitudinal connecting members. In one particularly preferred embodiment, the frame comprises two undulating hoop members joined by two pairs of proximal longitudinal connecting members and two pairs of distal longitudinal connecting members, where the longitudinal connecting members have substantially the same length and the circumferential space between each pair of longitudinal connecting members is less than about 10% of the total length of the longitudinal connecting members. Circumferentially adjacent pairs of closely spaced longitudinal can be staggered with respect to one another. The third longitudinal connecting strut 330 is staggered with respect to the first longitudinal connecting strut 310 and the second longitudinal connecting strut 320. The second longitudinal connecting strut 320 is positioned at a first circumferential distance 510 from the first longitudinal connecting strut 310, and a second circumferential distance 520 from the third longitudinal connecting strut 330. Preferably, two longitudinal connecting members are closely positioned such that the circumferential distance between a pair of closely spaced longitudinal connecting members is less than the circumferential distance between either of the individual closely spaced longitudinal connecting members and the other circumferentially adjacent longitudinal connecting members. For example, the first circumferential distance 510 is preferably about 15% of the second circumferential distance 520 such that the second longitudinal connecting strut 320 is positioned circumferentially closer to the first longitudinal connecting strut 310, than to the longitudinally adjacent third longitudinal connecting strut 330.

In a third embodiment, each strut of the undulating hoop member is oriented with respect to a longitudinal connecting member to define a strut angle between the longitudinal connecting strut and the connected strut. The strut angle is measured between two undulating hoop members. Unless otherwise noted, reference to strut angles are measured within the space between two longitudinally adjacent hoop members. In FIG. 3, the intersection of the first longitudinal connecting member 310 and the first strut 130 of the proximal undulating hoop segment 100 defines a first strut angle 430. When the longitudinal connecting members are parallel to each other and longitudinally adjacent strut segments of longitudinally adjacent undulating hoop members are parallel to each other, the intersection of each strut of the proximal undulating hoop member 100 with each longitudinal connecting member 300 defines a strut angle that is congruent with the first strut angle 430, including first distal strut angle 432 and second distal strut angle 434. The first strut angle 430 and the first distal strut angle 432 are preferably substantially equal. The first strut angle 430 is preferably between about 145° and 155°, most preferably about 148-149°. A strut angle can also be between about 90° and 180°, including about 95°, 100°, 105°, 110°, 115°, 120°, 125°, 130°, 135°, 140°, 145°, 150°, 155°, 160°, 165°, 170°, or 175°, or more, as well any interval of 0.5° therebetween, and more preferably between about 135°, 140°, 145°, 150°, 155°, 160° or 165°. Preferably, a frame is characterized by a plurality of substantially equal strut angles within each undulating hoop member, and/or between different undulating hoop members.

Figure 4:
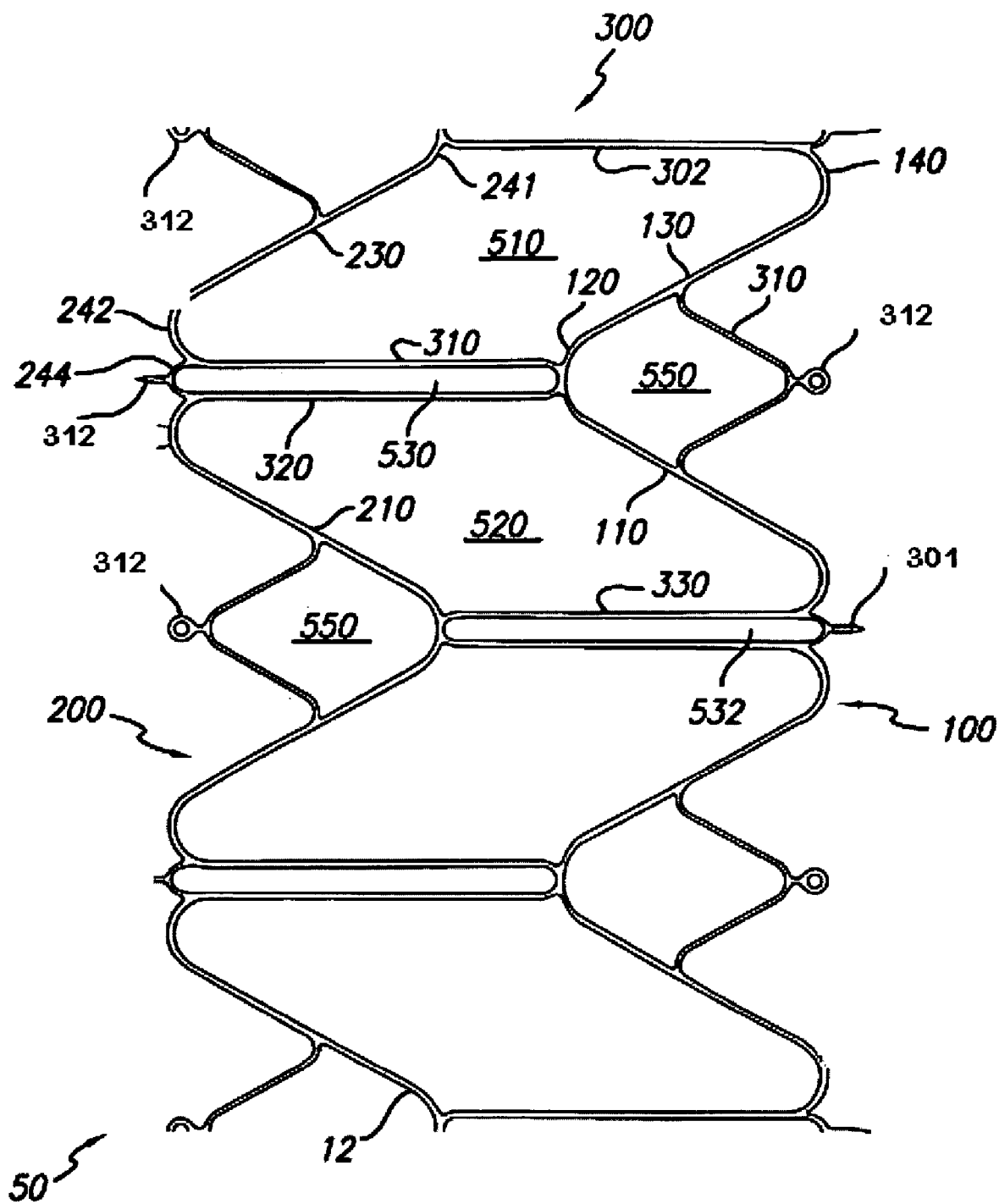
FIG. 4 is a third flat plan view of a first implantable frame.

The implantable frames can comprise a plurality of curved and straight member portions that together define an interior lumen extending along a longitudinal axis between a proximal end and a distal end. Preferably, the interior lumen and the exterior surface are both substantially cylindrical. The implantable frames can have an exterior surface comprising a plurality of openings between the interior lumen and the exterior surface. The openings are preferably bounded by portions of the implantable frame. Preferably, the implantable frame comprises a plurality of interstitial openings. An interstitial opening is bounded by two undulating hoop members and two longitudinal connecting members. The term "bounded" is used to indicate that at least a portion of the opening is defined by the portions of the specified portions of the frame. FIG. 4 shows a flat plan view 50 of the implantable frame 12 defining three types of openings bounded by a pair of parallel longitudinal connecting struts, a portion of a proximal undulating hoop member and a portion of a distal undulating hoop member. The implantable frame 12 includes the proximal undulating hoop member 100 connected to the distal undulating hoop member 200 by a plurality of longitudinal connecting members 300, as shown in FIG. 1A-C and FIG. 3. Interstitial openings are bounded by portions of two undulating hoop members and two longitudinal connecting members.

Preferably, the interstitial openings are perimetrically defined on the distal and proximal ends by strut and bend portions of adjacent distal and proximal undulating hoop members, respectively, and the two lateral sides by a first and a second circumferentially adjacent longitudinal connecting members. Most preferably, circumferentially adjacent longitudinal connecting members are longitudinally staggered. For example, with reference to FIG. 4, a first interstitial opening 510 is perimetrically defined by portions of the distal undulating hoop member 200 (a portion of a fifth bend 241, the first strut 230, and a first bend 242), the first longitudinal connecting member 310, portions of the proximal undulating hoop member 100 (a portion of the second bend 120, the first strut 130, and the first bend 140), and a fourth longitudinal connecting member 302.

In a fourth embodiment, the implantable frame defines pairs of interstitial openings having mirror image configurations with respect to one another. Preferably, the frame comprises an integer number of pairs of interstitial openings that are symmetrical to each other. Each interstitial opening can be positioned across the interior lumen from a symmetrical interstitial opening. For example, a second interstitial opening 520 is bounded by portions of the distal undulating hoop member 200 and the proximal undulating hoop member 100, the second longitudinal connecting member 320 and the third longitudinal connecting member 330. The second interstitial opening 520 is a mirror image of the first interstitial opening 510.

The implantable frame can also define one or more load abatement openings. A load abatement opening is bounded by two closely spaced, circumferentially adjacent longitudinal connecting members and a portion of two undulating hoop members. Preferably, a load abatement opening is perimetrically defined by a bend in a first undulating hoop member connected to two paired longitudinal connecting members that are also connected to a bend of a second undulating hoop member. More preferably, the paired longitudinal connecting members bounding the load abatement opening are substantially of the same length, width and cross sectional area and are circumferentially separated from each other at a distance that is less than 25%, 20%, 19%, 18%, 17%, 16%, 15%, 14%, 13%, 12%, 11%, 10%, 9%, 8%, 7%, 6%, 5%, 4%, 3%, 2%, or 1% of the total length of the longitudinal connecting members. Preferably, the load abatement opening is bounded by two paired longitudinal attachment members of equal length that are circumferentially spaced at a distance that is about 25%, or more preferably 20% or 15%, or most preferably about 10% or less of the total length of the longitudinal connecting members. Referring to FIG. 4, a first load abatement opening 530 is perimetrically defined by a portion of the first bend 120 of the proximal undulating hoop member 100, the first longitudinal connecting member 310, the second bend 244 of the distal undulating hoop member 200, and the second longitudinal connecting member 320. Some embodiments provide a plurality of load abatement openings. Preferably, the frame bounds multiple load abatement openings having substantially the same surface area. Each load abatement opening in FIG. 4, including a second load abatement opening 532, are congruent to the first load abatement opening 530. In some embodiments, an implantable frame bounds proximal and distal load abatement openings bounded by paired proximal longitudinal connecting members and distal longitudinal connecting members, respectively. Preferably, the implantable frame has (n) pairs of mirror image interstitial openings and (n) pairs of identical load abatement openings, where (n) is an integer of 1 to 12, preferably 1 to 6 and most preferably 2 or 3. Frame 12 has four load abatement openings in the assembled configuration 20 in FIG. 1B.

Figure 5A:
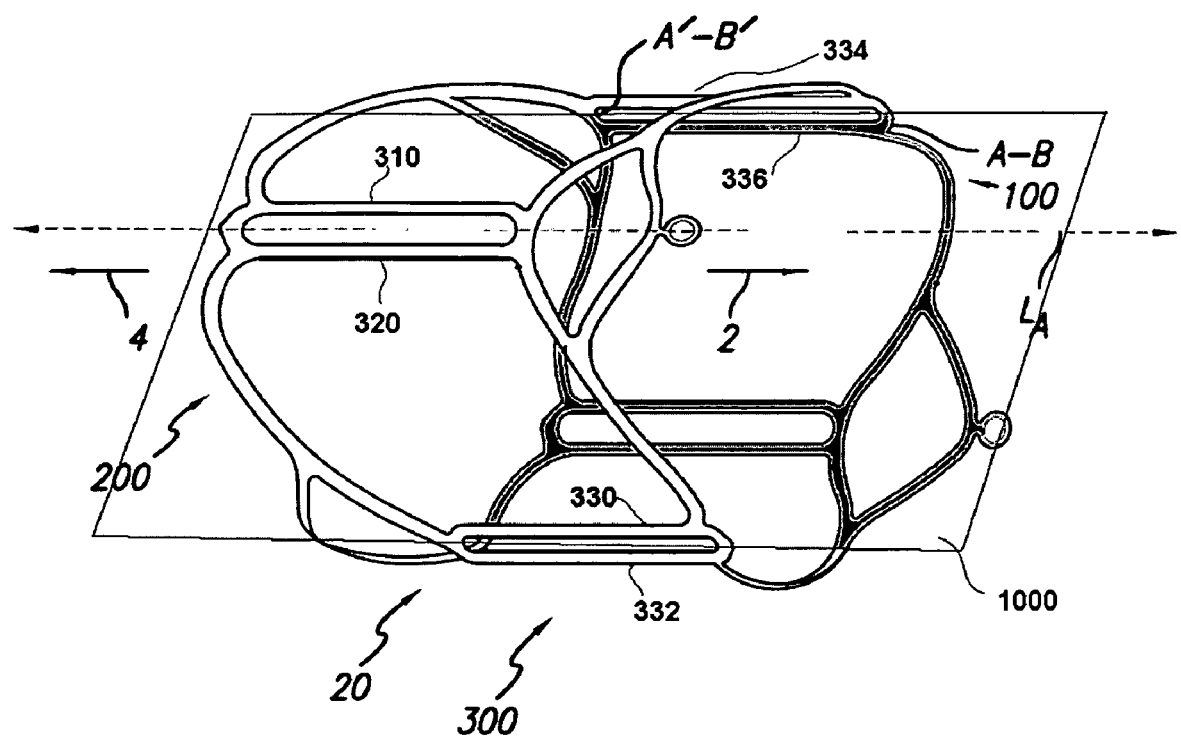
FIG. 5A is a perspective view of the assembled first implantable frame of FIG. 1A in the assembled configuration, showing a first symmetry plane.
Figure 5B:
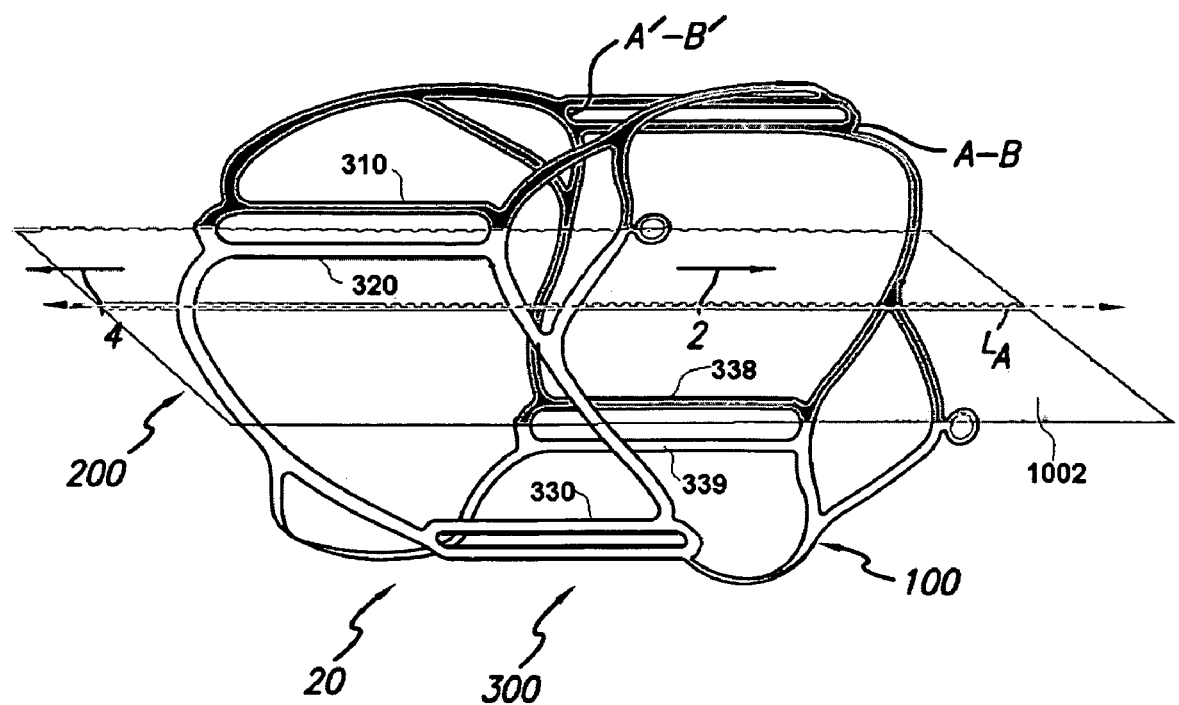
FIG. 5B is a perspective view of the assembled first implantable frame of FIG. 1A in the assembled configuration, showing a second symmetry plane.

In a fifth embodiment, the implantable frame is characterized by two or more symmetry planes containing the longitudinal axis of the implantable frame. Preferably, each symmetry plane contains the longitudinal axis of the frame in the expanded configuration. Most preferably, each symmetry plane contains the longitudinal axis of the frame in the expanded configuration and bisects a longitudinal connecting member. The circumference of the implantable frame can comprise non-adjacent interstitial openings having mirror image configurations, and non-adjacent identical load abatement openings. The frame 12 has two symmetry planes containing the longitudinal axis $L_A$. FIGS. 5A and 5B show the two symmetry planes containing the longitudinal axis $L_A$ of the frame 12 in the assembled configuration 20, identical to the frame 12 shown in FIG. 1B. FIG. 5A shows a first symmetry plane 1000 containing the longitudinal axis $L_A$, and extending between the third longitudinal connecting member 330 and a longitudinal connecting member 332, and between a longitudinal connecting member 334 (positioned across the lumen from the third longitudinal connecting member 330) and a longitudinal connecting member 336 (positioned across the lumen from the longitudinal connecting member 332). Portions of the frame 12 above the first symmetry plane 1000 are in white, and portions of the frame 12 below the first symmetry plane 1000 are shaded. FIG. 5B shows a second symmetry plane 1002 containing the longitudinal axis $L_A$, and extending between the first longitudinal connecting member 310 and the second longitudinal connecting member 320, as well as between a longitudinal connecting member 338 (positioned across the lumen from the first longitudinal connecting member 310) and a longitudinal connecting member 339 (positioned across the lumen from the second longitudinal connecting member 320). Portions of the frame 12 in front of the second symmetry plane 1002 are in white, and portions of the frame 12 behind the second symmetry plane 1002 are shaded. The first symmetry plane 1000 intersects the second symmetry plane 1002 along the longitudinal axis $L_A$, and both planes are orthogonal (oriented at 90 degrees) to one another. The implantable frame preferably has (m) symmetry planes, where (m) is preferably an integer of 1 to 6, more preferably 1 to 3 and most preferably 2 or 3. The implantable frame also preferably has the same number of pairs of mirror image interstitial openings and symmetry planes containing the longitudinal axis. In some embodiments, implantable frames have (x) distal struts, (x) proximal struts and (x/2) symmetry planes in the expanded configuration each containing the longitudinal axis, where (x) is an integer of 2 to 12, preferably 2, 4, 6, 8, or 10. Preferably, the implantable frame has (2i) symmetry planes containing the longitudinal axis, and (4i) to (8i) longitudinal connecting members, where (i) is any integer equal to 1 or greater. The first frame 12 in the assembled configuration 20 has four distal struts (x=4) and two symmetry planes (m=x/2), a total of eight total struts (y=8) and eight longitudinal connecting members, the distal hoop member has six distal bends (n=6) and two proximal bends (n/3), and the proximal hoop member has six proximal bends (n=6) and two distal bends (n/3).

Frame Configuration Variations

Figure 6A:
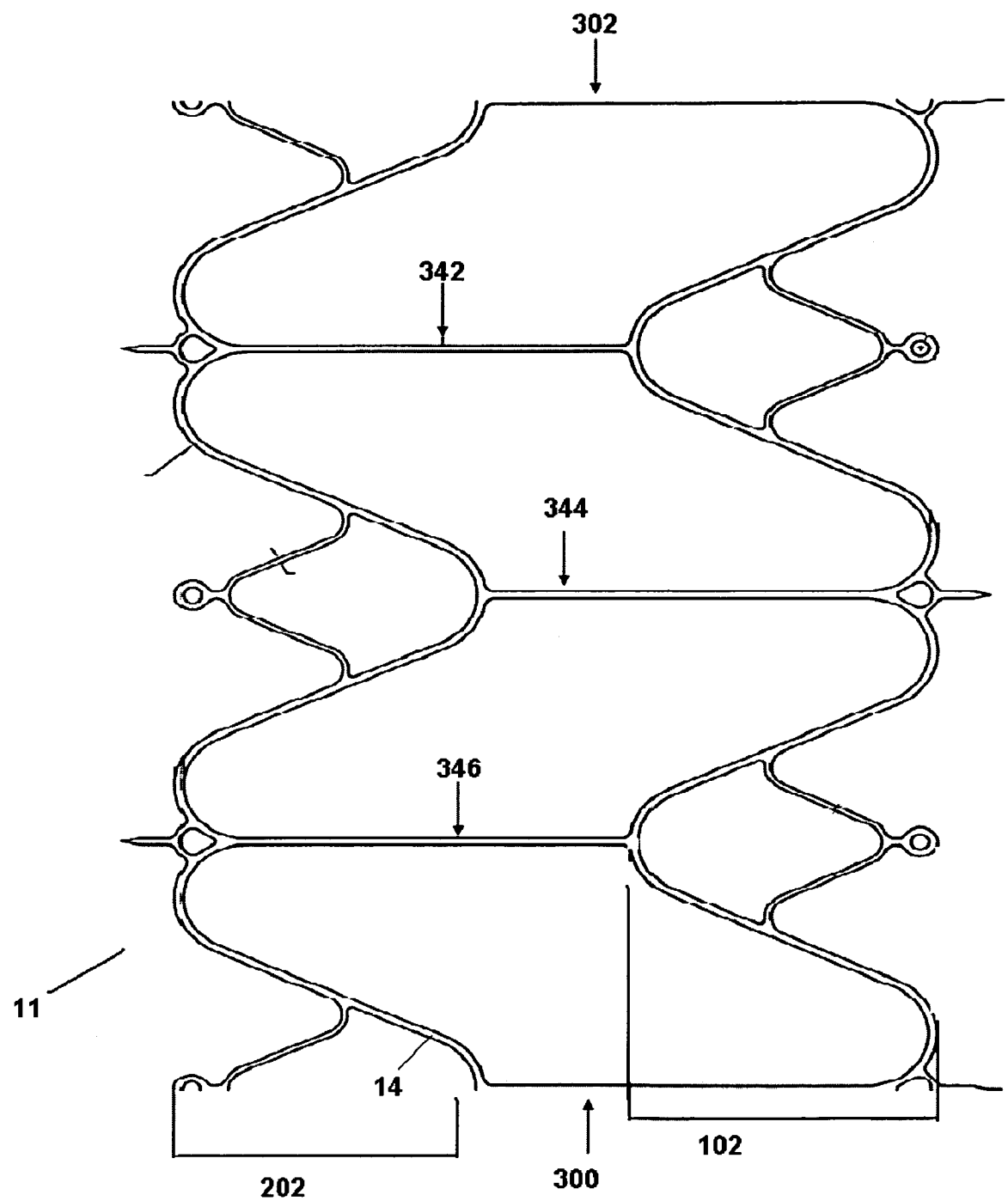
FIG. 6A is a first flat plan view of a second implantable frame.
Figure 6B:
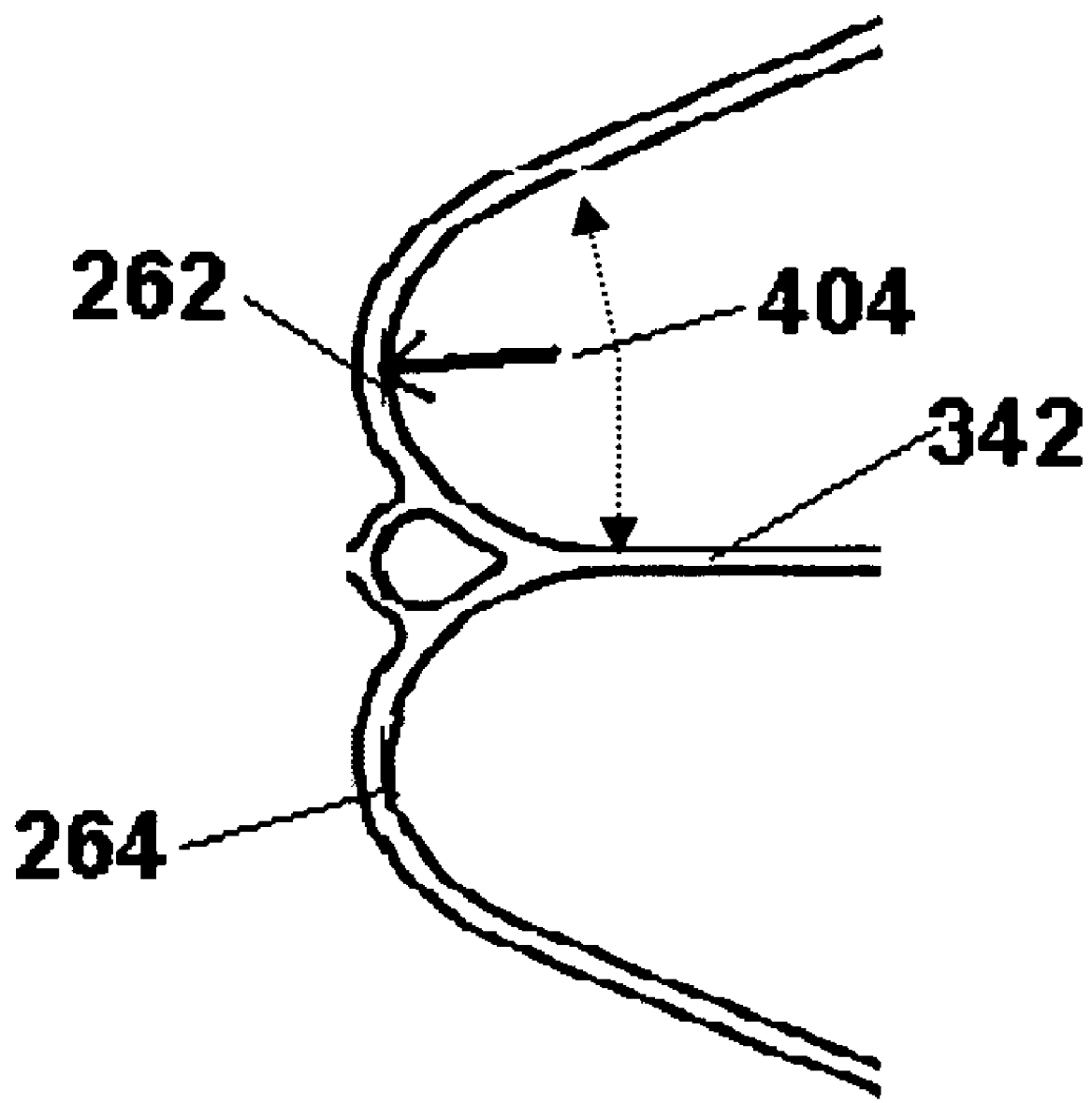
FIG. 6B is a detailed view of a portion of the first implantable frame of FIG. 6A.

FIG. 6A shows a flat plan view 11 of a second frame 14 comprising four longitudinal connecting struts 302 connecting a distal undulating hoop member 202 to a proximal undulating hoop member 102. The second frame 14 is identical to the first frame 12 in FIGS. 1A-C, except with respect to the number and position of the longitudinal connecting struts 302. The undulating hoop members 102, 202 together comprise eight struts (y=8) and the second frame 14 comprises y/2, or 4 longitudinal connecting members. In the first frame 12, all of the longitudinal connecting members 300 are arranged as closely spaced pairs, whereas in the second frame 14, all of the longitudinal connecting members 302 are evenly spaced with respect to circumferentially adjacent longitudinal connecting members. For example, a second longitudinal connecting strut 344 is circumferentially adjacent to both a first longitudinal connecting strut 342 and a third longitudinal connecting strut 346. Other frames can be formed by substituting one or more of the longitudinal connecting members 302 in the second frame 14 with a pair of closely spaced longitudinal connecting members, as in the first frame 12. FIG. 6B shows a detailed view of a portion of the second frame 14, showing a first bend 262 and a second bend 264 connected to a portion of the first longitudinal connecting member 342. The first bend 262 extends from the first strut 250 to the first longitudinal connecting member 342 and has a semi-circular configuration forming an arc at a first hypothetical radius 404. The first hypothetical radius 404 is positioned between the proximal hoop member 202 and the distal hoop member 102 (which are shown in FIG. 6A). The arc of the first bend 262 preferably subtends an angle of between about 5 and 45 degrees between the first longitudinal connecting member 342 and the first strut 250, including angles of about 10, 15, 20, 25, 30, 35, and 40, but preferably about 15-35 degrees.

Figure 7A:
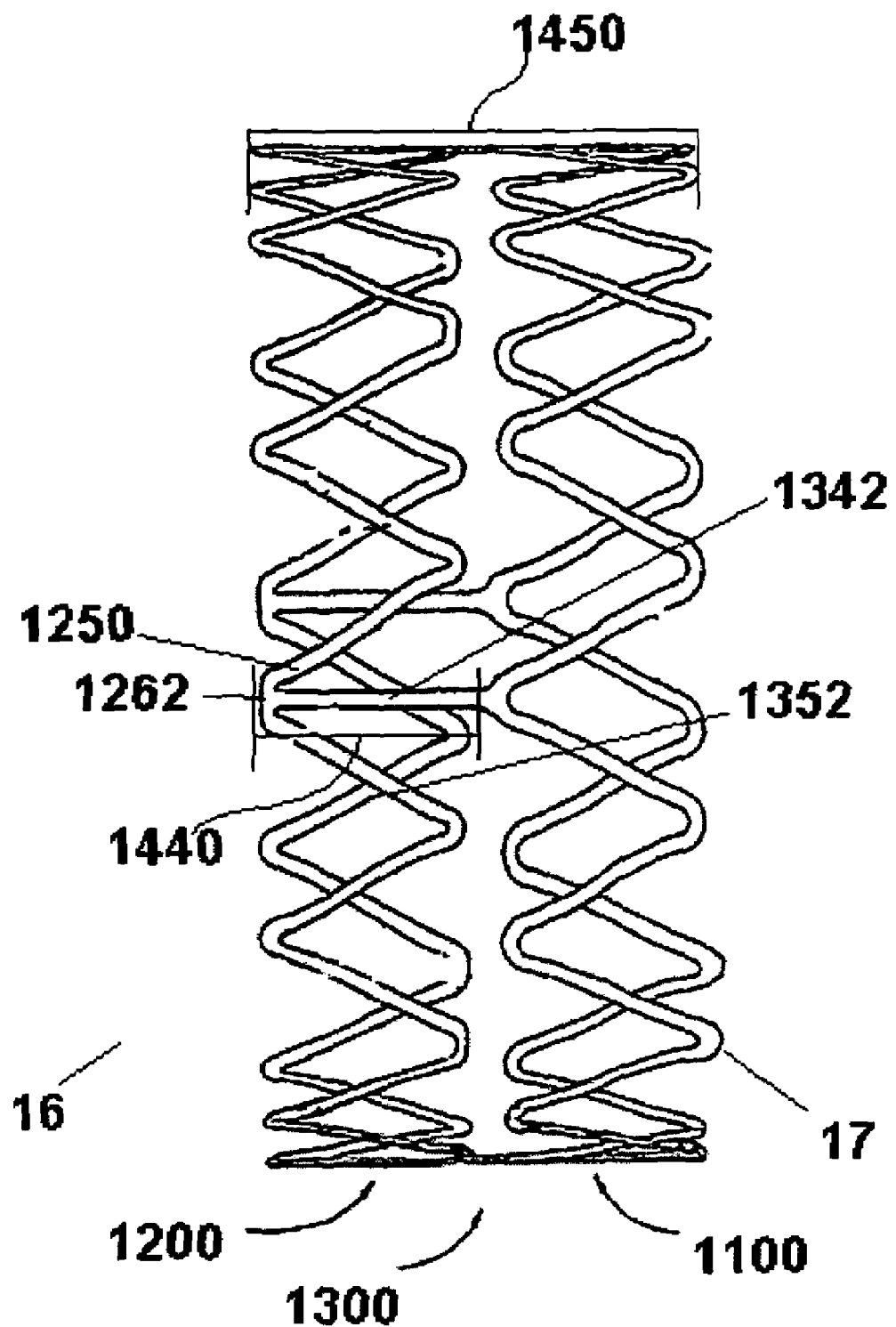
FIG. 7A is a perspective view of a third implantable frame.
Figure 7B:
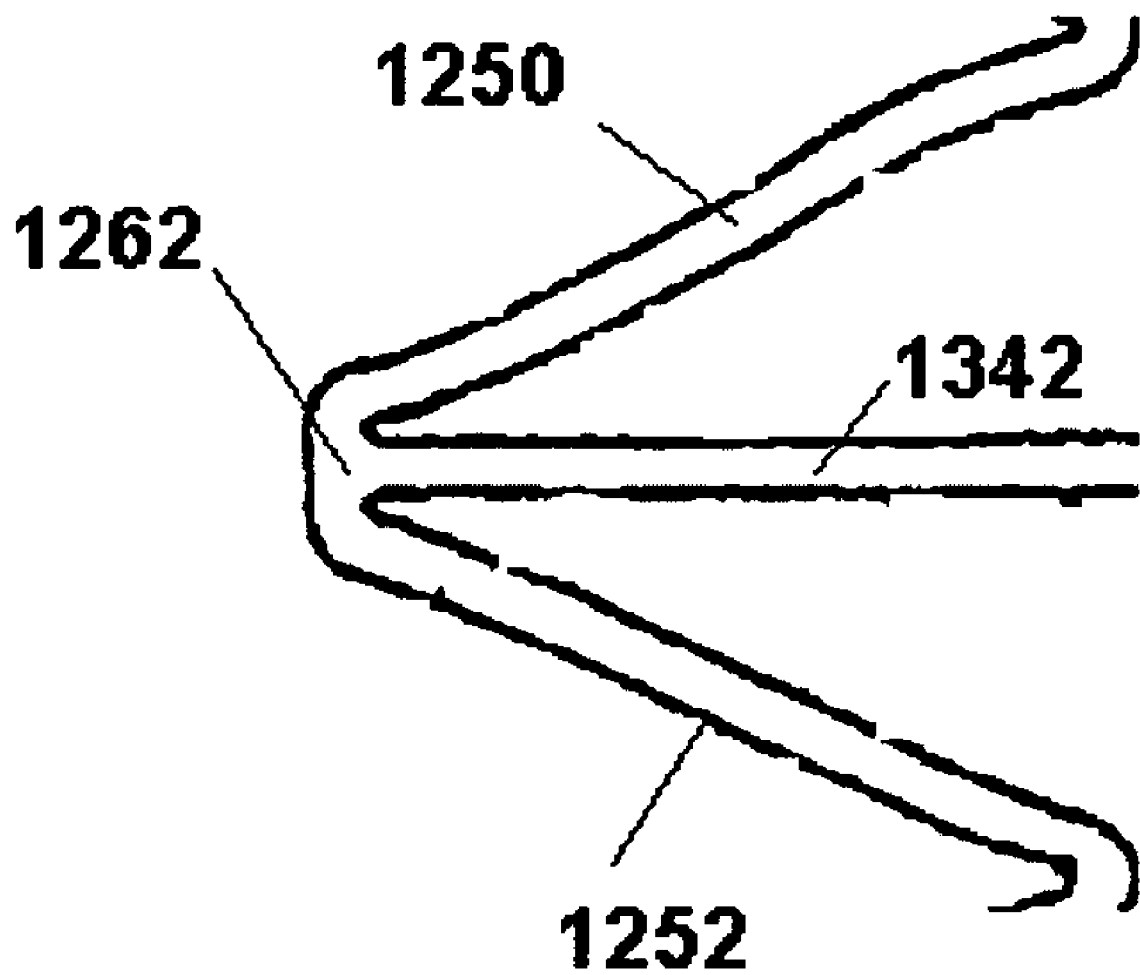
FIG. 7B is a detailed view of a portion of the first implantable frame of FIG. 7A.

FIG. 7A shows a flat plan view 16 of a third frame 17, comprising four longitudinal connecting struts 1300 connecting a distal undulating hoop member 1200 to a proximal undulating hoop member 1100. Each of the longitudinal connecting struts 1300 have equal lengths. The length 1440 of the longitudinal connecting struts 1300 can be any length suitable for implantation in a body vessel, such as about 10-15 mm. The length 1450 of the third frame 17 is measured along the longitudinal axis of the frame 17 from the inflection point of the most distal bend of the distal undulating hoop member 1200 to the inflection point of the most proximal bend of the proximal undulating hoop member 1100. Preferably, the inflection points of the distal bends of each hoop member are all longitudinally aligned with respect to each other. The length 1450 of the third frame 17 is preferably between about 1.5 and 2.0 times the length 1440 of the longitudinal connecting members 1300. The length 1450 of the implantable frame 17 is about 2.0 times the length 440 of the longitudinal struts 300 (i.e., the ratio of the length 1450 of the implantable frame 17 to the length 1440 of the longitudinal struts 1300 is about 2.00). Optionally, the frame 12 can also include additional hoop members positioned between the proximal hoop member 100 and the distal hoop member 200. Other frames can be formed by substituting one or more of the longitudinal connecting members 1302 in the third frame 17 with a pair of closely spaced longitudinal connecting members, as in the first frame 12. FIG. 7B shows a detailed view of a portion of the second frame 14, in a radially expanded state, showing a first bend 1262 connected to a portion of a first longitudinal connecting member 1342 a first strut 1250 and a second strut 1252. The third frame 17 bends are configured as three-way, acute angular junctions between circumferentially adjacent struts and a longitudinal connecting member, instead of as arcuate arc segments. The first bend 1262 does not have a semi-circular arc configuration, but preferably forms substantially equal angles of between about 5 and 45 degrees (including angles of about 10, 15, 20, 25, 30, 35, and 40, but preferably about 15-35 degrees) between the first longitudinal connecting member 1342 and the first strut 1250, and between the first longitudinal connecting member 1342 and the second strut 1252.

While many of the illustrative embodiments provide implantable frames with two undulating hoop members, other embodiments comprising three or more undulating hoop members. Additional undulating hoop members are preferably longitudinally aligned with a proximal and a distal undulating hoop member by being centered on a common longitudinal axis in the expanded assembled frame configuration. Teachings related to implantable frames comprising one or more undulating hoop members can be applied by one of skill in the art to make and use implantable frames with two, three or more undulating hoop members each preferably joined by one or more longitudinal connecting members.

The frame can have any size suitable for intralumenal implantation. The length of the frame measured along the longitudinal axis is preferably from up to 50 mm, or preferably between 5 mm and 50 mm or higher, including 5, 6, 7, 8, 9, 10, 11, 12, 13, 14, 15, 16, 17, 18, 19, 20, 21, 22, 23, 24, 25, 26, 27, 28, 29, 30, 30, 32, 34, 35, 36, 38, 40, 42, 44, 45, 46, 48 and 50 mm, and any increment of 0.25 mm or 0.10 mm increment thereof. Some preferred embodiments have lengths of 8, 12, 13, 16, 20, 23, 24, 25, 28, 32 or 33 mm.

The diameter of the expanded configuration of the implantable frame can be selected by one skilled in the art given the desired location for implantation. When in the compressed state for delivery to a desired location within a body lumen, an implantable frame is typically reduced from about two to about six times the diameter of the stents when in their expanded configuration before compression. For example, typical implantable frames may have a compressed external diameter of about 1 millimeter to about 3 millimeters for delivery and an expanded external diameter in a body lumen of about 3 millimeters to about 20 millimeters when released from compression in a large body vessel. Some implantable frames used in veins may have a compressed external diameter of about 1.00, 1.20, 1.25, 1.40, 1.50, 1.60, 1.75, 1.80, 2.00, 2.20, 2.25, 2.30, 2.40, 2.50, 2.60, 2.75, 2.80, 2.90, 3.00 mm or more and an expanded external diameter of up to about 20 mm, including between about 1 and 20 mm. Some implantable frames, for example for arterial body vessels, preferably have external diameters of 2.00, 2.20, 2.25, 2.30, 2.40, 2.50, 2.60, 2.70, 2.75, 2.80, 2.90, 3.00, 3.10, 3.20, 3.25, 3.30, 3.40, 3.50, 3.60, 3.70, 3.75, 3.80, 3.90, 4.00, 4.20, 4.25, 4.30, 4.40, 4.50, 4.60, 4.70, 4.75, 4.80, 4.90, 5.00 mm, or increments of 0.25, 0.10, 0.05 or 0.01 mm between these diameters. Other preferred embodiments, for example for implantation in veins, have expanded external diameters of between about 3 to about 25 mm, including external diameters of 3, 4, 5, 6, 7, 8, 9, 10, 11, 12, 13, 14, 15, 16, 17, 18, 19, 20, 21, 22, 23, 24, 25 mm, or any increments of 0.25, 0.10, 0.05 or 0.01 mm between these diameters. In certain preferred embodiments, the implantable frame has an expanded inner diameter of 1.25, 2.00, 2.50, 2.75, 3.00, or 3.50 mm. Table 1 below provides various dimensions of diameter and circumference for preferred frames having the configuration 20 shown in FIG. 1B, including frames having two different ratios between the length of the longitudinal connecting members and the total frame length.

TABLE 1

Preferred Frame Dimensions

| Length of longitudinal connecting members (mm) (α) | Overall frame length (mm) (β) | Ratio of (β/α) | Diameter of Frame (mm) | Circumference of Frame (mm) |
|---|---|---|---|---|
| 12.73 | 21.00 | 1.65 | 9.00 | 28.27 |
| 12.73 | 21.00 | 1.65 | 9.50 | 29.85 |
| 12.73 | 21.00 | 1.65 | 10.00 | 31.42 |
| 12.73 | 21.00 | 1.65 | 10.50 | 32.99 |
| 12.73 | 21.00 | 1.65 | 11.00 | 34.56 |
| 12.73 | 21.00 | 1.65 | 11.50 | 36.13 |
| 12.73 | 21.00 | 1.65 | 12.00 | 37.70 |
| 14.89 | 25.00 | 1.68 | 11.00 | 34.56 |
| 14.89 | 25.00 | 1.68 | 11.50 | 36.13 |
| 14.89 | 25.00 | 1.68 | 12.00 | 37.70 |
| 14.89 | 25.00 | 1.68 | 12.50 | 39.27 |
| 14.89 | 25.00 | 1.68 | 13.00 | 40.84 |
| 14.89 | 25.00 | 1.68 | 13.50 | 42.41 |
| 14.89 | 25.00 | 1.68 | 14.00 | 43.98 |

The cross sectional shape of the implantable frame can be selected by one skilled in the art for particular applications, and can have the same or different shapes throughout the implantable frame or portions thereof. Suitable cross sectional dimensions of an implantable frame or portion thereof can be selected based on a variety of factors, including the intended use of the device, the material and design of the device, and other relevant concerns. The frame forming the undulating hoops, longitudinal connecting struts, or bridging members can have the same or different cross sectional shape(s). In one embodiment, the implantable frame has a square, trapezoidal, circular, triangular or rectangular cross sectional shape. Preferably, the undulating hoop members and the longitudinal connecting struts both have similar cross sectional dimensions. Suitable dimensions for each side of a square or rectangular cross section, or for the diameter of a circular cross section, range from 0.001-inch (0.0254 mm) to about 0.100-inch (2.54 mm). Preferably, the longest cross sectional dimension of an implantable frame member is between about 0.001-inch (0.0254 mm) and 0.0049-inch (0.1245 mm). In one embodiment, one side of a rectangular or square cross sectional area (or diameter of a circular cross sectional area) is between about 0.004-inch (0.102 mm) and about 0.010-inch (0.254 mm). In some embodiments, at least a portion of the frame has a strut thickness of 0.0022, 0.0025, 0.0027, 0.0036, 0.0037, 0.0049, 0.005, 0.0055, 0.006, or 0.009-inch. For example, one preferred embodiment has an implantable frame with a width of 0.2286 mm (0.0090-inch) along the external surface of the implantable frame along the undulating hoop members and the longitudinal connecting members. In some embodiments, the implantable frame can comprise bridging members with a width of about 0.0060-inch or 0.0090-inch. In one preferred embodiment, the implantable frame has a length of 25.00 mm and an external outer diameter of 12.50 mm in the expanded configuration, and an outer diameter of 3.0 mm in the compressed delivery configuration.

Intralumenal Frame Delivery

The implantable frames are designed to be percutaneously delivered through a body lumen to a target site. The target site may be, for example, a location in the venous system adjacent to an insufficient venous valve. The implantable frames may be delivered, for example, on their own or as part of an implantable prosthetic valve.

An appropriately sized delivery catheter can be selected by one skilled in the art for a given application. For example, some embodiments can be delivered using a delivery catheter selected from one or more delivery catheter sizes from the group consisting of: 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 french (F) delivery catheters, or increments of 0.1 F therebetween. In some embodiments, a delivery catheter sized between 1 and 25 F, or preferably between about 1.5 F and 5 F can be used, preferably a 1.8 F (0.60 mm), 2.0 F (0.66 mm), 2.3 F (0.75 mm), 2.6 F (0.85 mm), 2.7 F (0.9 mm), 2.9 F (0.95 mm), or 3.3 (1.10 mm) delivery catheters.

Implantable frames or prostheses comprising the implantable frame can be delivered into a body lumen using a system which includes a catheter. In some embodiments, implantable frames can be intralumenally delivered inside the body by a catheter that supports the implantable frame in a compacted form as it is transported to the desired site, for example within a body vessel. Upon reaching the site, the implantable frame can be expanded and securably placed within the body vessel, for example by securably engaging the walls of the body vessel lumen. The expansion mechanism may involve forcing the stent to expand radially outward, for example, by inflation of a balloon formed in the distal portion of the catheter, to inelastically deform the stent and fix it at a predetermined expanded position in contact with the lumen wall. The expansion balloon can then be deflated and the catheter removed. In another technique, the implantable frame is formed of an elastic material that will self-expand after being compacted. During introduction into the body, the implantable frame is restrained in the compacted condition. When the stent has been delivered to the desired site for implantation, the restraint is removed, allowing the implantable frame to self-expand by its own internal elastic restoring force. Once the implantable frame is located at the constricted portion of the lumen, the sheath is removed to expose the stent, which is expanded so it contacts the lumen wall. The catheter is subsequently removed from the body by pulling it in the proximal direction, through the larger lumen diameter created by the expanded prosthesis, which is left in the body.

In some embodiments, the implantable frames impart radially outward directed force during deployment, whether self-expanding or radially-expandable. The radially outward directed force can serve to hold the body lumen open against a force directed radially inward, as well as preventing restriction of the passageway through the lumen by intimal flaps or dissections generated by, such as prior balloon angioplasty. Another function of the radially outward directed force can also fix the position of the stent within the body lumen by intimate contact between the stent and the walls of the lumen. Preferably, the outwardly directed force does not traumatize the lumen walls.

The implantable frames can be placed in any medically appropriate location for a given application. For example, in some embodiments, the implantable frame can serve as part of a venous valve prosthetic and be implanted in the femoral vein, including at the proximal (groin), mid (mid section) or distal (adjacent to the knee) portions of the vein.

Frame Materials

Preferred materials for frames include those materials that can provide the desired functional characteristics with respect to mechanical load bearing, biological compatibility, modulus of elasticity, radio-opacity, or other desired properties. For some embodiments, the materials used to form the implantable frames can comprise a material that exhibits excellent corrosion resistance. For some embodiments, the material can be selected to be sufficiently radiopaque and create minimal artifacts during magnetic resonance imaging techniques (MRI). In some embodiments, the implantable frame can comprise a metal, a metal alloy, a polymer, or any suitable combination thereof, for example as frame with multiple layers.

Preferably, the implantable frames are self-expanding stents comprising a material capable of significant recoverable strain to assume a low profile for delivery to a desired location within a body lumen. After release of the compressed self-expanding stent, it is preferred that the frame be capable of radially expanding back to its original diameter or close to its original diameter. Accordingly, some embodiments provide frames made from material with a low yield stress (to make the frame deformable at manageable balloon pressures), high elastic modulus (for minimal recoil), and is work hardened through expansion for high strength. Particularly preferred materials for self-expanding implantable frames are shape memory alloys that exhibit superelastic behavior, i.e., are capable of significant distortion without plastic deformation. Frames manufactured of such materials may be significantly compressed without permanent plastic deformation, i.e., they are compressed such that the maximum strain level in the stent is below the recoverable strain limit of the material. Discussions relating to nickel titanium alloys and other alloys that exhibit behaviors suitable for frames can be found in, e.g., U.S. Pat. No. 5,597,378 (Jervis) and WO 95/31945 (Burmeister et al.). A preferred shape memory alloy is Ni—Ti, although any of the other known shape memory alloys may be used as well. Such other alloys include: Au—Cd, Cu—Zn, In—Ti, Cu—Zn—Al, Ti—Nb, Au—Cu—Zn, Cu—Zn—Sn, CuZn—Si, Cu—Al—Ni, Ag—Cd, Cu—Sn, Cu—Zn—Ga, Ni—Al, Fe—Pt, U—Nb, Ti—Pd—Ni, Fe—Mn—Si, and the like. These alloys may also be doped with small amounts of other elements for various property modifications as may be desired and as is known in the art. Nickel titanium alloys suitable for use in manufacturing implantable frames can be obtained from, e.g., Memory Corp., Brookfield, Conn. One suitable material possessing desirable characteristics for self-expansion is Nitinol, a Nickel-Titanium alloy that can recover elastic deformations of up to 10 percent. This unusually large elastic range is commonly known as superelasticity.

In some embodiments, the implantable frames are designed to be expanded by a balloon or some other device (i.e., the frames are not self-expanding), and may be manufactured from an inert, biocompatible material with high corrosion resistance that can be plastically deformed at low-moderate stress levels, such as tantalum. The implantable frames can be deployed by both assisted (mechanical) expansion, i.e. balloon expansion, and self-expansion means. In embodiments where the implantable frame is deployed by mechanical (balloon) expansion, the implantable frame is made from materials that can be plastically deformed through the expansion of a mechanical assist device, such as by the inflation of a catheter based balloon. When the balloon is deflated, the frame can remain substantially in the expanded shape. Other acceptable materials include stainless steel, titanium ASTM F63-83 Grade 1, niobium or high carat gold K 19-22. One widely used material for balloon expandable structures is stainless steel, particularly 316L stainless steel. This material is particularly corrosion resistant with a low carbon content and additions of molybdenum and niobium. Fully annealed, stainless steel is easily deformable. Alternative materials for mechanically expandable structural frames that maintain similar characteristics to stainless steel include tantalum, platinum alloys, niobium alloys, and cobalt alloys.

In addition, the frames may be formed from or coated with other materials, such as polymers and bioabsorbable polymers may be used for the implantable frames. In one embodiment, the implantable frame is formed from 316L stainless steel. In another embodiment, the implantable frame is formed from a cobalt chromium alloy. The implantable frames can also comprise (that is, be formed from or coated with) a variety of polymers with limited bioabsorbability, including polyethylene (PE); polypropylene (PP); polyisobutylene; poly(alpha olefin); alkyl (alkyl)acrylates such as poly (n-butyl methacrylate) (PBMA) poly(methyl acrylate) or poly(methyl methacrylate) (PMMA); poly(ethyl acrylate); parylenes such as parylene C; ethyl vinyl acetate (EVA); poly(ethylene-co-vinyl acetate) (PEVA), or copolymers or mixtures thereof.

For some embodiments, it is desirable to provide implantable frames comprising bioabsorbable polymers. Bioabsorbable materials absorb into the body after a period of time. The period of time for the structural frame to absorb may vary, but is typically sufficient to allow desired biological processes such tissue growth to occur at the implant location. The implantable frames can comprise one or more bioabsorbable materials. A wide variety of bioabsorbable materials are known in the art, as well as equivalents thereof, can be used to form implantable frame. Nonlimiting examples of bioabsorbable polymers include polyesters such as poly(hydroxyalkanoates), poly(lactic acid) or polylactide (PLA), poly(glycolic acid) or polyglycolide (PGA), poly(caprolactone), poly (valerolactone) and co-polymers thereof; polycarbonates; polyoxaesters such as poly(ethylene oxalate), poly(alkylene oxalates); polyanhydrides; poly(amino acids); polyphosphazenes; phosphorylcholine; phosphatidylcholine; various hydrogels; polydioxanone, poly(DTE carbonate), and co-polymers or mixtures of two or more polymers. The implantable frames can also include various natural polymers such as fibrin, collagens, extracellular matrix (ECM) materials, dextrans, polysaccharides and hyaluronic acid.

The implantable frames or portions thereof can optionally comprise material that permits identification of the position or orientation of the frame within a body passage. Radiopaque markers are advantageously positioned at one or more ends of the implantable frame to aid the physician in positioning the frame at a site inside a body vessel. For example, portions of the implantable frame can include a radiopaque material that can be identified by X-rays. The frame can also comprise materials that are useful with contrast dyes to identify the frame within a body passage. The implantable frame 12 comprises a plurality of radiopaque markers 312 attached to the bridging members 310. Numerous materials known in the art, and equivalents thereof, can be used in the implantable frames to provide information about the frame in a body vessel. U.S. Pat. No. 6,409,752, issued Jun. 25, 2002 to Boatman et al., incorporated herein by reference, discloses various radiopaque materials that can be used in or on the implantable frames. Nonlimiting examples of radiopaque materials include, but are not limited to, high-density metals such as platinum, iridium, gold, silver, tantalum or their alloys, or radiopaque polymeric compounds. Preferably, radiopaque materials are highly visible under fluoroscopic illumination and are visible even at minimal thickness. In some preferred embodiments, the implantable frames comprise radiopaque material such as gold, platinum, tungsten, or iridium, as well as mixtures and alloys thereof, in an eyelet structure attached to one or more bridging members.

The disclosure of various materials for forming the structural frame should not be construed as limiting the scope of the invention. One of ordinary skill in the art would understand that other materials possessing similar characteristics may also be used in the construction of the implantable frame.

Methods of Manufacture

The implantable frames may be fabricated using any suitable method known in the art. Preferably, the complete frame structure is cut from a solid tube or sheet of material, and thus the frame would be considered a monolithic unit. Laser cutting, water-jet cutting and photochemical etching are all methods that can be employed to form the structural frame from sheet and tube stock. Still other methods for fabricating the complete frame structure as previously disclosed would be understood by one of skill in the art.

Alternatively, the frame can also be formed from wire using wire forming techniques, such as coiling, braiding, or knitting. By welding the wire at specific locations a closed-cell structure may be created. This allows for continuous production, i.e. the components of the implantable frame may be cut to length from a long wire mesh tube. In addition, an implantable frame is constructed from sheet, wire (round or flat) or tubing. The method of fabrication can be selected by one skilled in the art depending on the raw material used. Techniques for forming implantable frames are discussed, for example, in Dougal et al., "Stent Design: Implications for Restenosis," Rev. Cardiovasc Med. 3 (suppl. 5), S16-S22 (2002), which is incorporated herein by reference in its entirety.

In some embodiments, connections between the strut members and the bends in an undulating hoop member, as well as the connection between the undulating hoop member and the longitudinal connecting members, may be by welding or other suitable connecting means. Other connection means include the use of a binder, heat, or chemical bond, and/or attachment by mechanical means, such as pressing, welding or suturing. In addition, portions of the frame may be attached by applying a bonding coating.

An implantable frame can optionally be sterilized using any suitable technique known in the art, or equivalents thereto. For example, an implantable frame can be sterilized using ethylene oxide sterilization, as described in AAM/ISO 11135:1994 "Medical Devices—Validation and Routine Control of Ethylene Oxide Sterilization," incorporated herein by reference in its entirety. In some embodiments, a sterilized implantable frame satisfies a minimum Sterility Assurance Level (SAL) of about $10^{-6}$.

Vascular prostheses such as stent and stenugrafts undergo a number of different strain conditions in-vivo including: radial strain resulting from the applied diastolic and diastolic blood pressure, bending due to heart/limb movement and radial point loading due to limb motion or impact.

A variety of techniques can be used to measure and control the radial strains applied to vascular prostheses in bench-top simulators. A first technique involves applying a known volumetric fluid displacement to a vascular prosthesis that has been installed in a mock artery of known radial compliance. The volumetric displacement can be adjusted until the applied pressure closely simulates diastolic and diastolic conditions. The resulting radial strain can then be calculated as known in the art, for example with a formula that uses the volumetric displacement and mock artery dimensions. A second technique involves measuring the radial strain of the outside diameter of the mock artery using a laser micrometer. The internal radial strain can then be determined by multiplying the outside strain by a ratio that has been calculated using the outside and inside diameters and poison ratio of the mock artery material.

The implantable frames can be tested by placing them inside latex tubes filled with a phosphate buffered saline (PBS) solution and pulsating the tube volume to simulate physiological vessel compliance conditions (typically 3-5%). The tubes deflect radially with the applied pulsatile pressure. The tube-stent assembly acts as a mechanical system, producing strain levels comparable to the vessel-stent system of the human body. A laser transducer can be used to measure the tube dilation in real-time; WinTest uses the resulting signal to control the dilation within preset levels. At various intervals during the durability test, the devices can be removed and examined for mechanical integrity under a scanning electron microscope or with an endoscope assembly. A list of potential failure modes and potential tests that were identified by the MM I/ISO TG150, SC2, WG31 committee in developing their working document for endovascular devices, incorporated herein by reference.

For intravascular applications, the use of x-ray angiography, pressure catheters, or intravascular ultrasound provides a good means for determining the radial dilation and pressures that occur during each heartbeat or extraneous movement. Combining measured data with finite element modeling provides a better understanding of the test parameters that must be generated.

A variety of other test protocols can also be used. Information provided on the FDA Web site about previously approved devices can be useful in developing test protocols. Published papers and articles about applied loading in relevant publications, for example in the orthopedic and intravascular fields. For example, Conti et al., *Biomed Sci Instrum* 35:33946 (1999), incorporated herein by reference, discusses testing of intravascular implantable frames.

Kits comprising implantable frames are also provided. In one embodiment, a kit comprises an implantable frame and a delivery catheter.

Methods of Treatment

Implantable frames can be deployed at various locations and lumens in the body, such as, for example, coronary, vascular, nonvascular and peripheral vessels, ducts, and the like, including but not limited to cardiac valves, venous valves, valves in the esophagus and at the stomach, valves in the ureter and/or the vesica, valves in the biliary passages, valves in the lymphatic system and valves in the intestines. In one embodiment, a valve leaflet is attached to the frame to provide an implantable valve prosthesis that can be implanted within a vein, for instance, near an incompetent venous valve to treat venous valve insufficiency.

Methods of treatment preferably include the steps of loading an implantable frame, or a device comprising an implantable frame, in a compressed configuration into a delivery catheter, inserting the delivery catheter into a body vessel, translating the delivery catheter to a desired location, deploying the device comprising the implantable frame by securably placing the device in an expanded configuration at the desired location, and withdrawing the delivery catheter from the body vessel.

What is claimed is:

1. An implantable frame defining a substantially cylindrical lumen extending between a proximal end and a distal end along a longitudinal axis, the implantable frame having an exterior surface area with a plurality of openings, the implantable frame moveable between a compressed configuration and an expanded configuration, the implantable frame comprising:
 a proximal undulating hoop member having a plurality of struts and bends, a distal undulating hoop member having a plurality of struts and bends, and a plurality of longitudinal connecting members connecting the proximal undulating hoop member to the distal undulating hoop member;
 where the implantable frame comprises only two of the undulating hoop members, each of the proximal undulating hoop member and the distal undulating hoop member comprising a closed hoop structure formed by only four struts connected to each other by one or more bends:
 where each longitudinal connecting member is connected to at least one bend of the proximal undulating hoop member and at least one bend of the distal undulating hoop member, the implantable frame comprising at least four of the longitudinal connecting members:
 where each of the four struts is connected to the one or more bends adjacent to at least one of the longitudinal connecting members; and
 where the ratio between the length of the implantable frame and the length of the longitudinal connecting members is about 1.50 to about 2.00, the length of the implantable frame measured from the inflection point of the most distal bend in the distal hoop member and the inflection point of the most proximal bend in the proximal hoop member.

2. The implantable frame of claim 1, wherein the ratio is between about 1.65 and 1.75.

3. The implantable frame of claim 1, where the longitudinal connecting members have substantially equal length, and where the implantable frame comprises at least one closely-spaced pair of circumferentially adjacent longitudinal connecting members, where the distance between the closely paired longitudinal connecting members is less than about 25% of the length of the pair of longitudinal connecting members.

4. The implantable frame of claim 1, where the proximal undulating hoop member comprises a first strut and a second strut connected by a single bend, and further comprising a proximal bridging member connecting the first strut and the second strut.

5. The implantable frame of claim 1, wherein the implantable frame is self-expanding.

6. The implantable frame of claim 1, wherein the implantable frame in the expanded configuration is characterized by two or more symmetry planes containing the longitudinal axis of the implantable frame.

7. The implantable frame of claim 1, where the implantable frame comprises a plurality of substantially parallel longitudinal connecting members each having a substantially equal length and each extending between a proximal hoop member and a distal hoop member, including a first longitudinal connecting member circumferentially adjacent to a second longitudinal connecting member, the second longitudinal connecting member positioned between the first longitudinal connecting member and a third longitudinal connecting member, wherein
 a. the circumferential distance between the first longitudinal connecting member and the second longitudinal connecting member is less than about 25% of the length of the longitudinal connecting members; and
 b. the circumferential distance between the first longitudinal connecting member and the third longitudinal connecting member is greater than 25% of the length of the longitudinal connecting members.

8. The implantable frame of claim 1, where the proximal hoop member comprises a first strut, the plurality of longitudinal connecting members have a substantially equal length and include a first longitudinal connecting member extending between the proximal hoop member and the distal hoop member, and the proximal undulating hoop member comprises a first bend having a semi-circular configuration extending between the first longitudinal connecting member and the first strut, the first bend subtending an arc having a radius centered on the distal side of the proximal hoop member, where each longitudinal connecting member is substantially parallel to the longitudinal axis, and the first bend subtends an angle of between about 135° and about 175° between the first longitudinal connecting member and the first strut segment.

9. The implantable frame of claim 1, where the longitudinal connecting members have substantially equal length, and where the implantable frame comprises four closely-spaced pairs of circumferentially adjacent longitudinal connecting members, where one end of each pair of circumferentially adjacent longitudinal connecting members is connected to a single bend connecting two of the four struts of one of the undulating hoop members together and the other end of each pair of circumferentially adjacent longitudinal connecting members is connected to three bends connecting two of the four struts of the other undulating hoop member together, one of the three bends connecting the pair of circumferentially adjacent longitudinal connecting members together, and the other two of the three bends connecting one of the struts to one of the pair of circumferentially adjacent longitudinal connecting members, where each of the proximal undulating hoop member and the distal undulating hoop comprise two of the single bends and two of the three bends.

10. The implantable frame of claim 9, wherein the implantable frame is self-expanding.

11. The implantable frame of claim 10, where the distance between the closely paired longitudinal connecting members is less than about 25% of the length of the pair of longitudinal connecting members and the distance between adjacent pairs of longitudinal connecting members is greater than about 25% of the length of the pair of longitudinal connecting members.

12. The implantable frame of claim 11, wherein the ratio between the length of the implantable frame and the length of the longitudinal connecting members is about 1.65 and 1.75.

13. The implantable frame of claim 12, further comprising a proximal bridging member connecting each of the struts which are connected together with a single bend.

14. The implantable frame of claim 13, where the proximal hoop member comprises a first strut, the plurality of longitudinal connecting members have a substantially equal length and include a first longitudinal connecting member extending between the proximal hoop member and the distal hoop member, and the proximal undulating hoop member comprises a first bend having a semi-circular configuration extending between the first longitudinal connecting member and the first strut, the first bend subtending an arc having a radius centered on the distal side of the proximal hoop member, where each longitudinal connecting member is substantially parallel to the longitudinal axis, and the first bend subtends an angle of between about 135° and about 175° between the first longitudinal connecting member and the first strut segment.

15. The implantable frame of claim 14, wherein the implantable frame in the expanded configuration is characterized by two or more symmetry planes containing the longitudinal axis of the implantable frame.

16. The implantable frame of claim 1, where the longitudinal connecting members have substantially equal length; and where the implantable frame comprises only four longitudinal connecting members, where one end of each longitudinal connecting member is connected to a single bend connecting two of the four struts of one of the undulating hoop members together and the other end of each longitudinal connecting member is connected to two bends connecting two of the four struts of the other undulating hoop member together, each of the two bends connecting one of the struts to the longitudinal connecting member, where each of the proximal undulating hoop member and the distal undulating hoop comprise two of the single bends and two of the two bends.

17. The implantable frame of claim 16, wherein the implantable frame is self-expanding.

18. The implantable frame of claim 17, wherein the ratio between the length of the implantable frame and the length of the longitudinal connecting members is about 1.65 and 1.75.

19. The implantable frame of claim 18, further comprising a proximal bridging member connecting each of the struts which are connected together with a single bend.

* * * * *

UNITED STATES PATENT AND TRADEMARK OFFICE
CERTIFICATE OF CORRECTION

PATENT NO. : 7,658,759 B2  Page 1 of 1
APPLICATION NO. : 11/487629
DATED : February 9, 2010
INVENTOR(S) : Brian C. Case et al.

It is certified that error appears in the above-identified patent and that said Letters Patent is hereby corrected as shown below:

In the Claims

In column 25, claim 1, line 31, immediately after "bends" replace ":" with --;--.

In column 25, claim 1, line 36, immediately after "connecting members" replace ":" with --;--.

Signed and Sealed this

Thirteenth Day of April, 2010

David J. Kappos
*Director of the United States Patent and Trademark Office*